US012308097B2

(12) United States Patent
Bowers et al.

(10) Patent No.: US 12,308,097 B2
(45) Date of Patent: *May 20, 2025

(54) SYSTEMS AND METHODS OF EFFICIENTLY PERFORMING BIOLOGICAL ASSAYS

(71) Applicant: Becton, Dickinson and Company, Franklin Lakes, NJ (US)

(72) Inventors: Clarke Bowers, Baltimore, MD (US); William Howard Garrison, Cockeysville, MD (US); Michael T. VanSickler, Franklin Lakes, NJ (US); Michael Fenske, Stewartstown, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/523,768

(22) Filed: Nov. 29, 2023

(65) Prior Publication Data

US 2024/0105291 A1     Mar. 28, 2024

Related U.S. Application Data

(63) Continuation of application No. 18/163,789, filed on Feb. 2, 2023, now Pat. No. 11,887,703, which is a
(Continued)

(51) Int. Cl.
*G16H 10/40* (2018.01)
*G01N 35/00* (2006.01)
(Continued)

(52) U.S. Cl.
CPC ....... *G16H 10/40* (2018.01); *G01N 35/00623* (2013.01); *G01N 35/00663* (2013.01);
(Continued)

(58) Field of Classification Search
CPC ........ G16H 10/40; G16H 40/20; G16H 40/40; G16H 50/20; G16H 50/70;
(Continued)

(56) References Cited

U.S. PATENT DOCUMENTS 5,575,978 A * 11/1996 Clark ................... B01L 3/08
422/562
2008/0312893 A1* 12/2008 Denton ................. G16H 50/20
703/11
(Continued)

FOREIGN PATENT DOCUMENTS

JP         08-114600 A      5/1996
JP       2012-037346 A      2/2012
(Continued)

OTHER PUBLICATIONS

Anonymous, "Laboratory Information Management System", Wikipedia, Oct. 25, 2017, pp. 1-8 (Year: 2017).*
(Continued)

*Primary Examiner* — Joy Chng
(74) *Attorney, Agent, or Firm* — Knobbe, Martens, Olson & Bear LLP

(57) ABSTRACT

An automated laboratory system for processing biological samples in a batch type manner is disclosed. In one embodiment, the system may receive assay instructions for biological samples processing among a plurality of devices. The devices may include a pre-analytical instrument and one or more analysis systems. The system may include an orchestration core application for determining an order of performance for the assays ordered for the samples.

20 Claims, 20 Drawing Sheets

Related U.S. Application Data continuation of application No. 16/759,658, filed as application No. PCT/US2018/064221 on Dec. 6, 2018, now Pat. No. 11,581,089.

(60) Provisional application No. 62/626,581, filed on Feb. 5, 2018, provisional application No. 62/596,032, filed on Dec. 7, 2017, provisional application No. 62/596,052, filed on Dec. 7, 2017.

(51) Int. Cl.
| | |
|---|---|
| *G06Q 10/0631* | (2023.01) |
| *G16H 40/20* | (2018.01) |
| *G16H 40/40* | (2018.01) |
| *G16H 50/20* | (2018.01) |
| *G16H 50/70* | (2018.01) |

(52) U.S. Cl.
CPC ... *G01N 35/00871* (2013.01); *G01N 35/0092* (2013.01); *G06Q 10/06316* (2013.01); *G16H 40/20* (2018.01); *G16H 40/40* (2018.01); *G16H 50/20* (2018.01); *G16H 50/70* (2018.01); *G01N 2035/00643* (2013.01); *G01N 2035/0096* (2013.01)

(58) Field of Classification Search
CPC ....... G01N 35/00623; G01N 35/00663; G01N 35/00871; G01N 35/0092; G01N 2035/00643; G01N 2035/0096; G01N 2035/0094; G06Q 10/06316; G06Q 10/06393; G06T 7/00
USPC ............................................ 705/2–3; 702/19
See application file for complete search history.

(56) References Cited

U.S. PATENT DOCUMENTS

| | | |
|---|---|---|
| 2012/0039094 A1 | 12/2012 | Barnes |
| 2017/0021356 A1* | 1/2017 | Dority ................ G01N 35/1016 |
| 2017/0124263 A1* | 5/2017 | Crafts, Jr. .............. G16H 70/20 |

FOREIGN PATENT DOCUMENTS

| | | | |
|---|---|---|---|
| JP | 2012-075413 A | | 4/2012 |
| JP | 2014-199211 A | | 10/2014 |
| WO | WO 2017/143182 A2 | | 8/2017 |
| WO | WO 2017/184242 A2 | | 10/2017 |

OTHER PUBLICATIONS

Guder et al., "Glossary" in Diagnostic Samples: From The Patient to The Laboratory: The Impact of Preanalytical Variables on The Quality of Laboratory Results, Dec. 31, 2009, pp. 102-107 (Year: 2009).*

Anonymous "Laboratory information management system" Wikipedia, Oct. 25, 2017.

Guder, Walter, et al., "Glossary" in "Diagnostic Samples: from the Patient to the Laboratory: The Impact of Preanalytical Variables on the Quality of Laboratory Results" Dec. 31, 2009.

Extended European Search Report mailed Jul. 9, 2021 in corresponding European Patent Application No. PCT/US18/64221, filed Apr. 16, 2020.

International Search Report mailed Feb. 4, 2019 in corresponding International Application No. PCT/US18/64221, filed Dec. 6, 2018.

\* cited by examiner

SYSTEMS AND METHODS OF EFFICIENTLY PERFORMING BIOLOGICAL ASSAYS

RELATED APPLICATIONS

The present application is a continuation of U.S. patent application Ser. No. 18/163,789, filed Feb. 2, 2023, which is a continuation of U.S. patent application Ser. No. 16/759,658, filed Apr. 27, 2020, now issued as U.S. Pat. No. 11,581,089, issued on Feb. 14, 2023, which is a U.S. national phase application under 35 U.S.C. § 371 of International Application No. PCT/US2018/064221, filed Dec. 6, 2018 and published in English as WO 2019/113296 on Jun. 13, 2019, which claims priority under 35 U.S.C. § 119(e) to U.S. Provisional Application No. 62/596,052, filed on Dec. 7, 2017; U.S. Provisional Application No. 62/596,032, filed on Dec. 7, 2017; and U.S. Provisional Application No. 62/626,581, filed on Feb. 5, 2018. The content of each of these related applications is incorporated herein by reference in its entirety.

BACKGROUND

Field

The present disclosure relates generally to the field of diagnosis automation and more particularly automated orchestration of biological assays.

Description of the Related Art

Diagnostic testing of biological samples is instrumental in the health care industry's efforts to quickly and effectively diagnose and treat disease. Clinical laboratories that perform such diagnostic testing may receive hundreds or thousands of samples on a daily basis with an ever increasing demand. The challenge of managing such large quantities of samples may be assisted by the automation of sample analysis. Automated sample analysis is typically performed by automated analyzer instruments that are commonly self-contained systems which perform multistep processes on the biological samples to obtain diagnostic results.

Automated clinical analyzer instruments offer a user an array of automated tests that may be performed on a provided sample. However, when samples arrive at the laboratory, they are often not ready for analysis. In order to prepare a sample for testing with an automated analyzer instrument, a laboratory technician typically transfers an aliquot of the sample from a primary container or tube, as received by the laboratory, to a secondary container or tube which is amenable to the analyzer instrument. In addition, the technician typically may need to know what tests are to be performed on the sample so that the technician may select a test-specific reagent or diluent to be paired with the sample. This may be time consuming and may lead to operator error and exposure to communicable diseases.

Pre-analytical instruments meant to help prepare a sample for analysis and further remove the technician from the orchestration between the laboratory's receipt of a sample and the analyzer instrument's test results also exist. However, many of these instruments still require significant technician involvement, such as prior to loading samples in the pre-analytical instrument, once the samples have been prepared by the pre-analytical instrument, and once the analyzer instruments have completed analysis.

For example, some pre-analytical instruments may automatically transfer an aliquot of a sample from a first container to a second container. However, such systems often require a technician to manually pair identification codes of the first and second containers prior to loading them into the system, which may be time consuming and is prone to error.

In addition, many of these systems are not capable of being integrated with one or more analyzer instruments. In this regard, a technician may need to be present to manually transfer the samples from the pre-analytical instrument to an analyzer instrument and from the analyzer instrument to a storage location once analysis is complete. This redirects skilled labor to menial tasks and may create distractions in that the technician must be ever mindful of the progress of the samples within the pre-analytical instrument and analyzer instrument so that the technician is prepared to transfer samples when ready in order to minimize downtime.

Moreover, current pre-analytical instruments and analyzer instruments generally process samples in a continuous stream as they are introduced into the system. Thus, such systems process samples in a predefined sequence which is generally set by the user. In this regard, existing pre-analytical instruments generally do not take into account information other than what is provided by the user when deciding which sample to prepare next in the sequence. Furthermore, pre-analytical instruments typically prepare samples at different rates than the analyzer instruments which further complicate the integration between pre-analytical instruments and analyzer instruments. In this regard, a technician may be required to continuously keep track of samples prepared by the pre-analytical instrument until a full batch of samples is accumulated for manual transfer to an analyzer instrument. Alternatively, technicians may transfer partial batches to an analyzer instrument, which may reduce the analyzer instrument's productivity.

SUMMARY

Disclosed herein are systems and methods for running assays on biological samples and high throughput automation of biological assays. In one embodiment, the system comprises: a memory storing instructions; and a processor programmed by the instructions to execute a method comprising: receiving a plurality of assay instructions for a plurality of biological samples; determining the plurality of assays that need to be performed for each sample in the plurality of biological samples based on the assay instructions; determining the assay resources that are available to perform the plurality of assays; determining an order to perform each assay in the plurality of assays based on the assay resources that are available in order to maximize the efficiency of performing the plurality of assays; and instructing one or more analyzer instruments to carry out the plurality of assays based on the determined order.

In one embodiment, the method comprises: receiving a plurality of assay instructions for a plurality of biological samples; determining the plurality of assays that need to performed for each sample in the plurality of biological samples based on the assay instructions; determining the assay resources that are available to perform the plurality of assays; determining an order to perform each assay in the plurality of assays based on the assay resources that are available in order to maximize the efficiency of performing the plurality of assays; and instructing one or more analyzer instruments to carry out the plurality of assays based on the determined order.

In one embodiment, the system comprises a memory storing instructions; and a processor programmed by the instructions to execute a method comprising: receiving a plurality of assay instructions for a plurality of biological samples from a plurality of analysis systems; determining the plurality of assays that need to performed for each sample in the plurality of biological samples based on the assay instructions; identifying the analysis systems available to run each type of assay in the plurality of assays; determining the assay resources within the identified analysis systems that are available to perform the plurality of assays; determining an order to perform each assay in the plurality of assays based on the assay resources that are available in order to maximize the efficiency of performing the plurality of assays; and instructing one or more analysis systems to carry out specific assays of the plurality of assays based on the determined order.

In one embodiment, the system comprises: a first automated module configured to prepare a biological sample for at least one molecular assay; at least one second automated module for receiving the biological sample prepared by the first automated module and for performing a molecular assay on the received biological sample, wherein the first automated module and the second automated module each comprise at least one automated instruments; and an orchestration core computing device in communication with the first automated module, the second automated module and a laboratory information system, wherein the orchestration core computing device receives instructions for processing biological samples from the analysis system and manages the processing resources of the first and second automated devices where the orchestration core computing device comprises at least four processing layers, the first layer, which is in communication with the analysis system, being a service level object layer, an orchestration layer, an instrument module control layer and an instruments module layer, wherein the instruments module layer is in communication with the automated instruments in the first and second automated devices, and wherein the state of the automated instruments is communicated to the orchestration layer and based on the current state of the analysis systems, the orchestration core computing device groups two or more biological samples into a batch and communicates instructions to the instrument module layer for batch processing the samples.

DETAILED DESCRIPTION

Figure 1:
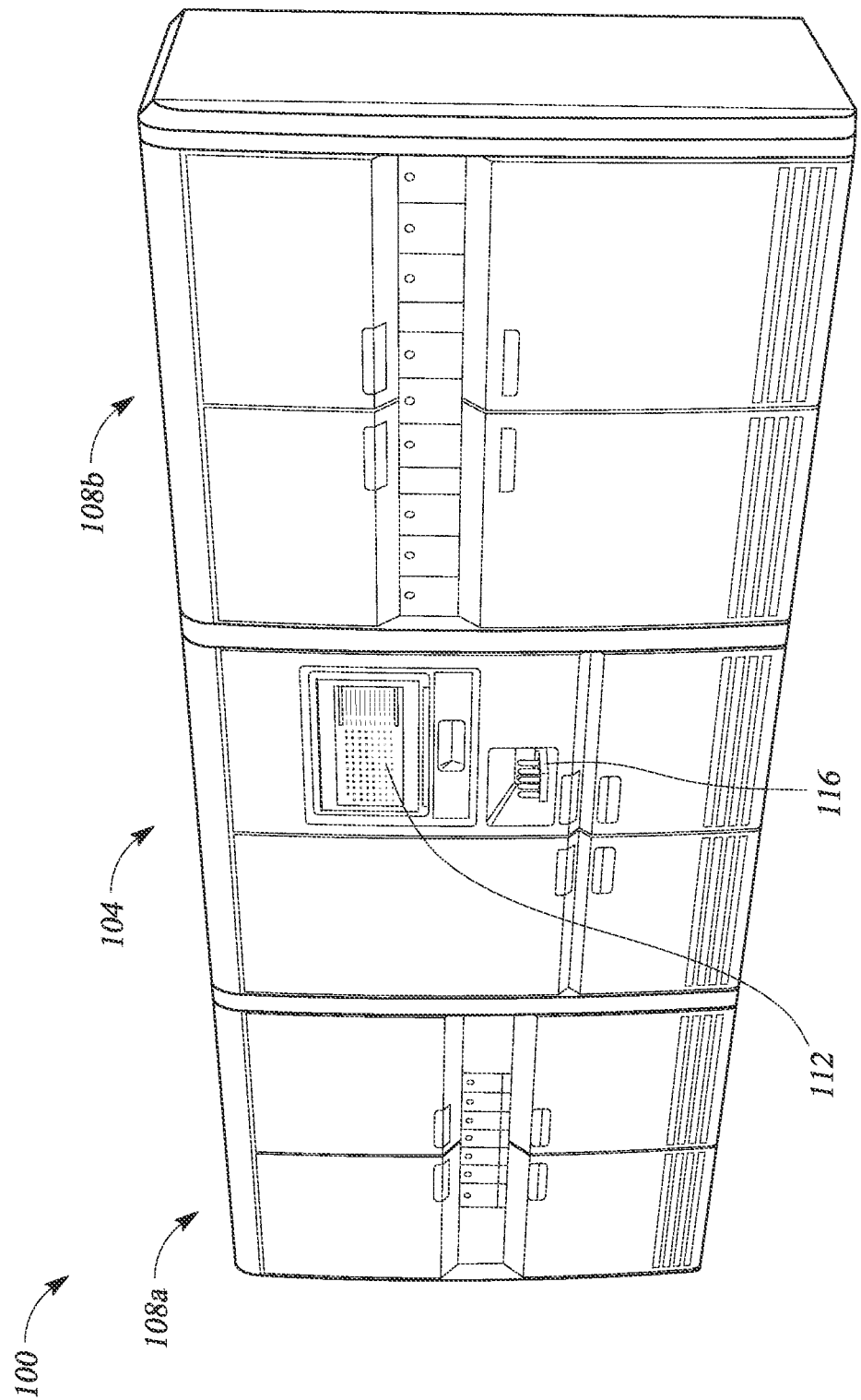
FIG. 1 is a perspective view of an analysis system according to one embodiment described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, may be arranged, substituted, combined, separated, and designed in a wide variety of different configurations, all of which are explicitly contemplated herein and made part of the disclosure herein.

Overview

The present disclosure describes devices, systems, and methods of performing processing and analysis of biological samples. In particular, a system architecture is described that coordinates automated sample processing among a plurality of analysis devices or systems having a high degree of automation. Inputs from a laboratory information system are received by an orchestration computing device that coordinates the operation of one or more analyzer and pre-analytical instruments to process samples in an informed and efficient manner to increase the overall efficiency of running assays on a plurality of analysis systems and analyzer instruments (also referred to as analyzers and assay devices). A variety of discrete inputs into the orchestration computing device are contemplated, the aggregate of inputs providing for efficient and expeditious sample processing with a minimum of operator inputs and interventions.

Sample Processing and Analysis System

FIG. 1 depicts an exemplary analysis system 100. The analysis system 100 can be an in vitro diagnostic system or include an in vitro diagnostic device. Such system, as depicted, includes a pre-analytical instrument 104, a first analyzer instrument 108a, and a second analyzer instrument 108b. The pre-analytical instrument 104 may include a user interface 112 for receiving user inputs and an input window 116 for receiving samples. Each of these units 104, 108a, and 108b is modular. Thus, the pre-analytical instrument 104 may be coupled to one or more analyzer instruments. In addition, each analyzer instrument that is in communication with the pre-analytical instrument 104 (both in terms of exchanging information and samples for processing) may perform the same or different operations. For example, the first analyzer instrument 108a may perform viral assays, such as human papilloma virus ("HPV") assays, while the second analyzer instrument 108b may perform bacterial and parasitic assays, such as those for detecting *Chlamydia trachomatis*, *Neisseria gonorrhea*, *Trichomonas vaginalis*, group B *streptococcus*, enteric bacteria, and enteric parasites. However, in some embodiments the analysis system 100 may be configured so that first and second analyzer instruments 108a, 108b are similar and capable of performing the same or similar assays. Such instrument modularity allows a clinical laboratory to tailor an analysis system 100 for its particular needs. An analysis system 100 is referred to herein as an electronic system.

The pre-analytical instrument 104 and analyzer instruments 108a, 108b each have hardware components that allow them to perform designated operations. For example, in one embodiment pre-analytical instrument 104 may be configured to pre-process biological samples so as to prepare the samples for analysis by the analyzer instruments 108a, 108b. In this regard, the pre-analytical instrument 104 may have tray/shuttle handling robots that are capable of transporting trays/shuttles of sample containers from one location to another within the instrument and to adjacent analyzer instruments, sample container manipulation robots that are capable of transporting and/or decapping individual sample containers, pipette robots that are capable of aspirating samples from one container and into another container, diluent dispensers for diluting samples, vortexers for vortexing samples, heat plates for warming samples, and cooling units for cooling samples. The analyzer instruments 108a, 108b may also have robotics that are capable of moving containers within their individual instruments, from the pre-analytical instrument 104, and back to the pre-analytical instrument 104. The analyzer instruments 108a, 108b may also include pipette robots, sample container manipulation robots, magnetic extractors (for providing a magnetic field to the sample container that is used (in conjunction with paramagnetic particles added to the sample) for sample purification), and any other hardware components that are needed for performing instrument operations.

In addition to the hardware components, the pre-analytical instrument 104 includes staging or accumulation areas. These areas are locations in which sample containers and other consumables are stored until they are designated for input into the workflow. These accumulation areas are in communication with the orchestration core application so that the orchestration core application may assign processing information to the sample so that the instrument may process the sample according to the instructions of the orchestration control application, as is described further below.

Figure 2A:
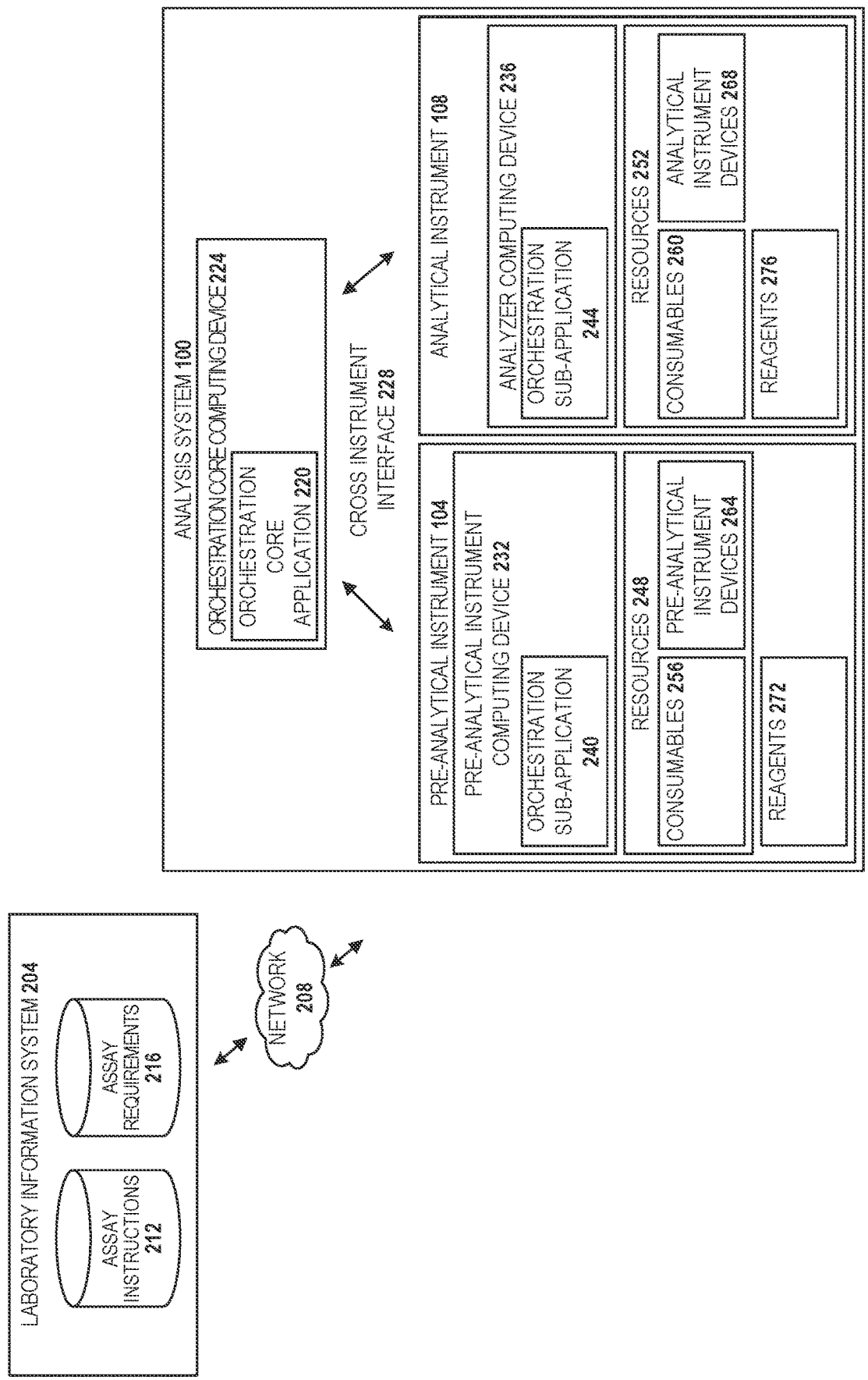
FIG. 2A is a block diagram of a distributed analysis system in communication with a laboratory information system according to one embodiment described herein.

FIG. 2A is a block diagram of an analysis system in communication with a laboratory information system according to one embodiment described herein. In one embodiment, an analysis system 100 may include at least one pre-analytical instrument 104 and one or more automated analyzer instruments 108. The pre-analytical instrument 104 may process the samples for analysis in the analyzer instruments 104. The analyzer instruments 108 may be configured to perform assays on biological samples while the pre-analytical instrument 104 may be configured to prepare samples for analysis by the analyzer instruments 108. For example, the pre-analytical instrument 104 may transfer a biological sample from one container to another container which is suitable for use by the analyzer instruments 108 and may also vortex, pre-warm, and cool the samples depending on the assays to be performed. Such analyzer instruments 108 and pre-analytical instrument 104 may each be modular standalone units that have robotics capable of transferring biological samples back and forth between the individual units when coupled together.

The analysis system 100 may be in communication with a laboratory information system 204 over a network 208. The laboratory information system 204 may be an existing information system that is operated by a healthcare facility or standalone clinical laboratory. Such laboratory information system may provide information regarding sample assay instructions 212, requirements for the assays ordered 216, and patient information to the analysis system. In some implementations, the analysis system 100 may receive patient information from a hospital information system.

The analysis system 100 may include an orchestration core application 220 executed by an orchestration core computing device 224 that communicates with the analyzer instruments 108 and the pre-analytical instrument 104 through a cross instrument interface 228, and the laboratory information system 204 through the network 208. The analysis system 100 may be behind a firewall or connect to the network 208 through another computing system to isolate the analysis system 100 and protect it from any incidental or malicious software that could impede or alter the performance of the analysis system 100.

The orchestration core application 220 may coordinate processes and manage resources among the one or more analyzer instruments 108 and the pre-analytical instrument 104 in order to achieve efficient uses of the available resources and keep the activity of those resources at or above a predetermined threshold level. The performance of the analysis system 100 may be determined based on a performance metric. For example, the performance metric may be a percentage of the maximal use of the processing resources available for the processing requirements at a given point in time. In addition, the orchestration core application 220 leverages information received from the laboratory information system 204, the analyzer instruments 108, and the pre-analytical instrument 104 to reduce, significantly reduce, or even eliminate operator involvement and to make high level decisions regarding activities that are to take place within each instrument based on ever-changing circumstances.

In one implementation, the computing devices 232, 236 of the pre-analytical instrument 104 and analyzer instruments 108 execute orchestration sub-applications 240, 244. Such orchestration sub-applications 240, 244 are linked to the orchestration core application 220 for implementing instructions provided by the orchestration core application 224. In this regard, decisions and instructions for implementing such decisions are communicated downward from the orchestration core application 220 to specific hardware components that perform the instructed actions. The instructions become more specific as they move down the chain from the orchestration core application to individual hardware devices. Information is also communicated upward from the individual hardware devices to the orchestration core application so that the orchestration core application frequently receives state updates which inform the decision-making process.

The orchestration core application 220 and the orchestration sub-applications 240, 244 may include state machines that operate on their own threads. In this regard, the core application 220 and the sub-applications 240, 244 may have lock down states that are used to make decisions so that a change in state does not interfere with the decision making process.

The orchestration core application 220 and orchestration sub-applications 240, 244 operate to achieve efficient use of the analytical instruments 108 and pre-analytical instrument 104. The goal is to obtain desired utilization of hardware resources within such instruments because idle time of system resources detracts from overall performance.

The orchestration core application 220 makes decisions based on the information from the laboratory information systems 204 regarding the biological samples that are to be processed and evaluated by the pre-analytical and analytical instruments 104, 108, respectively. The orchestration core application 220 organizes the individual biological samples into batches within the pre-analytical instrument 104, which helps maximize overall throughput. Samples are placed into a batch based on identity of processing conditions (e.g. thermocycling conditions) for the samples in the batch. To the extent possible, each sample in a batch is subjected to the same processing conditions (e.g. temperature, light frequencies). However, processing uniformity is not required. For example, if sample or control containers in a batch have already been pre-warmed, those samples will not be subjected to a pre-warming step. So not only is information about an individual sample "tracked" by the orchestration core application 220, information about the batch with which the individual sample is processed is also tracked. Said another way, there is a "one-to-many" relationship between the batch and the samples. Some information is specific to the samples and other information applies to each sample in the batch across the board.

In addition to implementing batch processing of samples, the orchestration core application 220 obtains a wide array of information inputs from a variety of sources in controlling and coordinating the processing resources 248, 252 of the pre-analytical and analytical instruments 104, 108. Such information includes the inventories of consumables 256, 260 for the instruments and the allocation of that inventory for the processes in queue, operational state of the instrument hardware, the assays ordered to be performed on the samples, sample availability; batches already in process, sample age, availability of the pre-analytical and analytical instruments 104, 108, availability of the instrument devices 264, 268 of the pre-analytical and analytical instruments 104, 108, biochemical stability of samples and reagents 272, 276, and the particular laboratory's business or compliance practices. The pre-analytical and analytical instruments 104, 108 are also referred to herein as instrument devices. In one embodiment, the analysis system 100 includes redundant hardware and consumables such that the analysis system 100 may keep operating while hardware is replaced and consumables are being replenished.

The orchestration core application 220 receives the assay instructions from a variety of different external systems such as the laboratory information system 204, a hospital information system, and another analysis system. In some implementations, the pre-analytical instrument 104 knows precisely what to do with the sample when it arrives in the pre-analytical instrument 104. Decisions regarding the actual processing may be largely pre-made. That is, decisions about batching, timing, assay and consumable resources required will all be factored in to the orchestration core application 220 by the time the sample arrives at the pre-analytical instrument.

The orchestration core application 220 may include three components: an orchestration state component, an orchestration decider component and an orchestration engine component. Each component has a distinct, assigned role in managing resources and controlling operation of the pre-analytical and analytical instrument devices 264, 268. The orchestration state component stores state information. The orchestration state component is configured to receive the operational state of the system hardware and instrument devices 264, 268. Therefore each instrument and submodule within each instrument is configured to communicate out information about its state and that state information is communicated to the orchestration state module either directly but, more typically, through the logic of the applicable instrument. The orchestration decider component uses the state information to make decisions. The orchestration engine component implements the decisions and guards the orchestration state component from being updated while a decision is being made.

In this regard, the orchestration core application 220 tracks consumable inventory. It is also configured to determine how much of the consumable quantity is allocated to batches being processed. Using such information, the orchestration core application 220 is configured to determine a net consumable inventory and make process flow determinations based upon the net amount of inventory to ensure samples are not process without consumable availability. In addition, the orchestration core application 220 is configured to notify a user that certain consumables need to be replenished in an instrument. Such consumables 256, 260 may include diluent, reagents, assay control samples, pipette tips, empty sample containers, extraction containers, and PCR plates, to name a few. Various sensors may be implemented to track such consumables 256, 260, such as a liquid level sensor for bulk diluent. Also, the orchestration core application 220 may keep track of a starting consumable inventory and how much of the consumables 256, 260 have been used from the start consumable inventor to determine a net value.

The orchestration core application 220 also tracks operational states of the analyzer instruments 108 and pre-analytical instrument 104 themselves. The orchestration core application 220 makes decisions on what samples may be processed and when the processing should start based on this information. The instrument devices 264, 268 may include physical hardware components such as motor encoders, integrated circuits, solenoids, and the like which help the orchestration core application 220 track the operational state of the hardware in each instrument. One aspect of an operational state is whether or not there is a failure or error in the operation of a particular component. In such event, the orchestration core application 220 is aware of redundant devices in the system and coordinates or activates such redundant devices in the event of component operational errors or failures. In this regard the orchestration core application 220 has pre-determined error protocols that it will execute in the event of a component operational error or failure. Another function performed by the orchestration core application 220 is to both understand the instruments, devices and individual components necessary to process a given batch and whether or not the hardware components, pre-analytical instruments, and analyzer instrument are currently engaged in or are allocated to a process.

The orchestration core application 220 communicates with one or more information systems to acquire sample assay instructions 212. Such systems may include hospital information systems, laboratory information systems 204, informatics systems and another analysis system. The orchestration core application 220 is configured to obtain this information as early as possible so that decisions about sample processing are made before the sample is actually scanned into the pre-analytical instrument 104. In this regard, a laboratory technician does not need to acquire sample assay order information, which reduces user error and frees the technician for other tasks.

The orchestration core application 220 is also configured to track the biological/chemical/mechanical lifetime of consumable inventory and samples, such as assay controls and reagents, and the biological samples themselves in various states of an assay protocol's execution. Exceeding limits of useful lifetime of samples and consumables may adversely affect the integrity of the assay results. Such lifetimes decrease as time advances and, if the age of a reagent or a sample exceeds a particular threshold, then the biochemistry of these reagents or samples may be altered. The orchestration core application 220 may prioritize samples in such a way that completion of assay protocol steps prior to a reagent or sample exceeding its lifetime is ensured.

The orchestration core application 220 may be further configured to receive information from the pre-analytical and analytical systems 104, 108 that will permit tracking the samples throughout their processing. This includes tracking sample aliquots obtained and dispensed to different containers for sample processing and sample transport from one instrument to another, such as sample transport from the pre-analytical instrument 104 to the analyzer instrument 108 (and back). This allows a laboratory technician to query the systems and instruments for sample location and its assay progress. If multiple assays are ordered for a single patient sample, the orchestration core application 220 coordinates and tracks execution of the multiple assays for the single sample without user intervention to maximize, or at least increase, the overall efficiency of carrying out the assays.

Figure 2B:
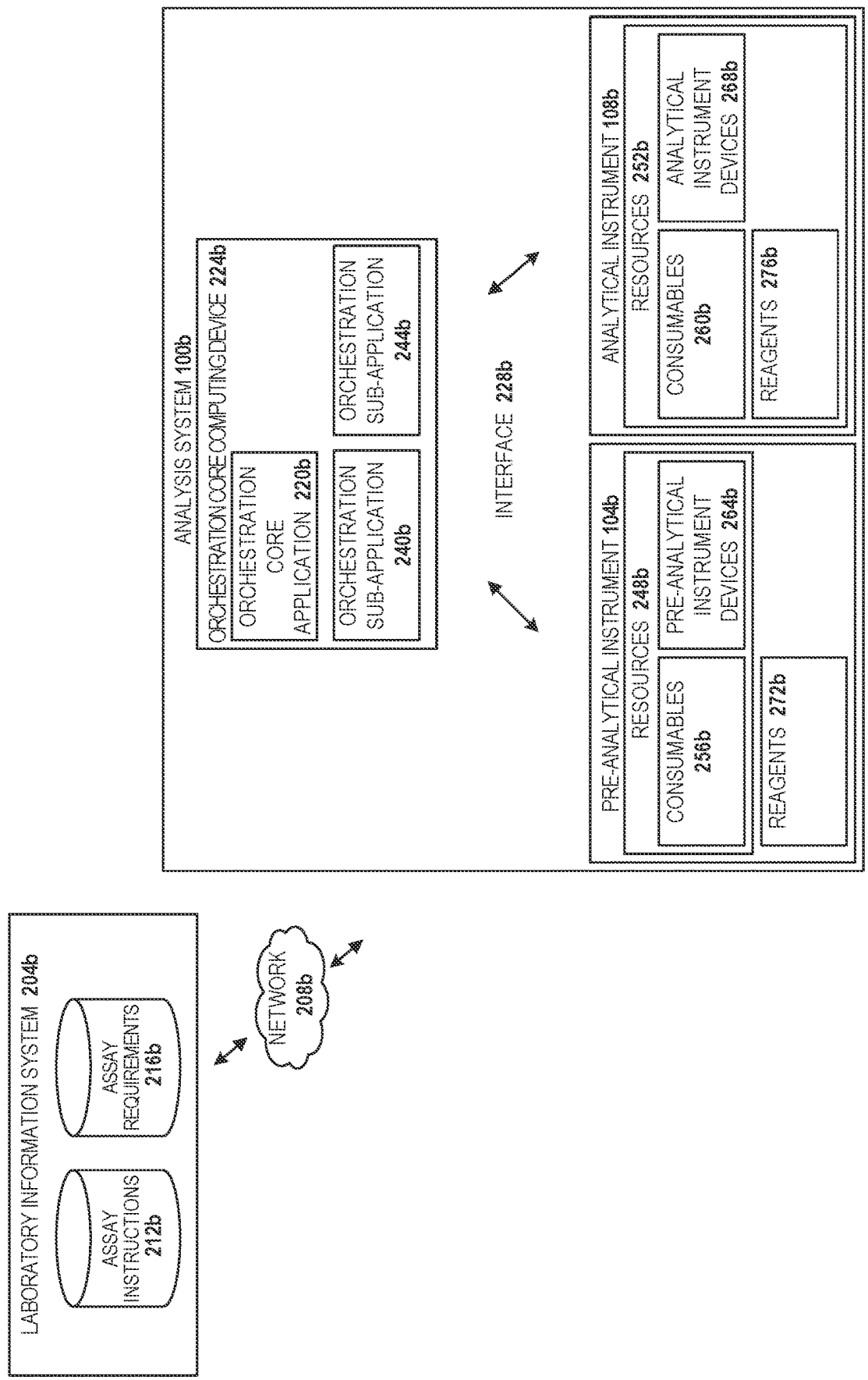
FIG. 2B is a block diagram of a centralized analysis system in communication with a laboratory information system according to one embodiment described herein.

FIG. 2B is a block diagram of a centralized analysis system 100b in communication with a laboratory information system according to one embodiment described herein. The analysis system 100b in FIG. 2B is similar to the analysis system 100 described with reference to FIG. 2A. As described in further details below, the analysis system 100b in FIG. 2B is a centralized system with the functions of the orchestration sub-applications 240b, 244b performed by the orchestration core computing device 224b.

In one embodiment, the analysis system 100b may include at least one pre-analytical instrument 104b and one or more automated analyzer instruments 108b. The pre-analytical instrument 104b may process the samples for analysis in the analyzer instruments 104b. The analyzer instruments 108b may be configured to perform assays on biological samples while the pre-analytical instrument 104b may be configured to prepare samples for analysis by the analyzer instruments 108b. The analysis system 100b may be in communication with a laboratory information system 204b over a network 208b. The analysis system 100b may include an orchestration core application 220b executed by an orchestration core computing device 224b that communicates with the analyzer instruments 108b and the pre-analytical instrument 104b through an interface 228b, such as a cross instrument interface, an inter-device interface, or an intra-device interface. The analysis system 100b may communicate with the laboratory information system 204b through the network 208b. The orchestration core application 220b may coordinate processes and manage resources among the one or more analyzer instruments 108b and the pre-analytical instrument 104b in order to achieve efficient uses of the available resources and keep the activity of those resources at or above a predetermined threshold level.

The orchestration core computing device 224b executes orchestration sub-applications 240b, 244b. Such orchestration sub-applications 240b, 244b are linked to the orchestration core application 220b for implementing instructions provided by the orchestration core application 220b. In this regard, decisions and instructions for implementing such decisions are communicated downward from the orchestration core application 220b to the orchestration sub-applications 240b, 244b to the specific hardware components that perform the instructed actions. The instructions become more specific as they move down the chain from the orchestration core application 220b to the orchestration sub-applications 240b, 244b to the individual hardware devices. Information is also communicated upward from the individual hardware devices to the orchestration core sub-applications 240b, 244b to the orchestration core application 220b so that the orchestration core application 224b and sub-applications 240b, 244b frequently receives state updates which inform the decision-making process.

The orchestration core application 220b and orchestration sub-applications 240b, 244b operate to achieve efficient use of the analytical instruments 108b and pre-analytical instrument 104b. The orchestration core application 220b makes decisions based on the information from the laboratory information systems 204b regarding the biological samples that are to be processed and evaluated by the pre-analytical and analytical instruments 104b, 108b, respectively. In addition to implementing batch processing of samples, the orchestration core application 220b obtains a wide array of information inputs from a variety of sources in controlling and coordinating the processing resources 248b, 252b of the pre-analytical and analytical instruments 104b, 108b. The orchestration core application 220b receives the assay instructions from a variety of different external systems such as the laboratory information system 204b, a hospital information system, and another analysis system.

The orchestration core application 220b may include three components: an orchestration state component, an orchestration decider component and an orchestration engine component. The orchestration core application 220b may track consumable inventory. The orchestration core application 220b also tracks operational states of the analyzer instruments 108b and pre-analytical instrument 104b themselves. The orchestration core application 220b is also configured to track the biological/chemical/mechanical lifetime of consumable inventory and samples, such as assay controls and reagents, and the biological samples themselves in various states of an assay protocol's execution. The orchestration core application 220b may be further configured to receive information from the pre-analytical and analytical systems 104b, 108b, via orchestration sub-applications 240b, 244b that will permit tracking the samples throughout their processing.

In the embodiment shown in FIG. 2B, the orchestration core application 220b, orchestration sub-application 240b, and orchestration sub-application 244b are illustrated as three components of the orchestration core computing device 224b. However, this is illustrative only and is not intended to be limiting. In another embodiment, the orchestration core computing device 224b may implement an orchestration core application 220b may perform the functionalities of the orchestration sub-applications 240b, 244b. In one embodiment, the orchestration core computing device 224b includes one orchestration sub-application that is linked to the orchestration core application 220b for implementing instructions provided by the orchestration core application 220b.

Orchestration Core System Architecture

Figure 3A:
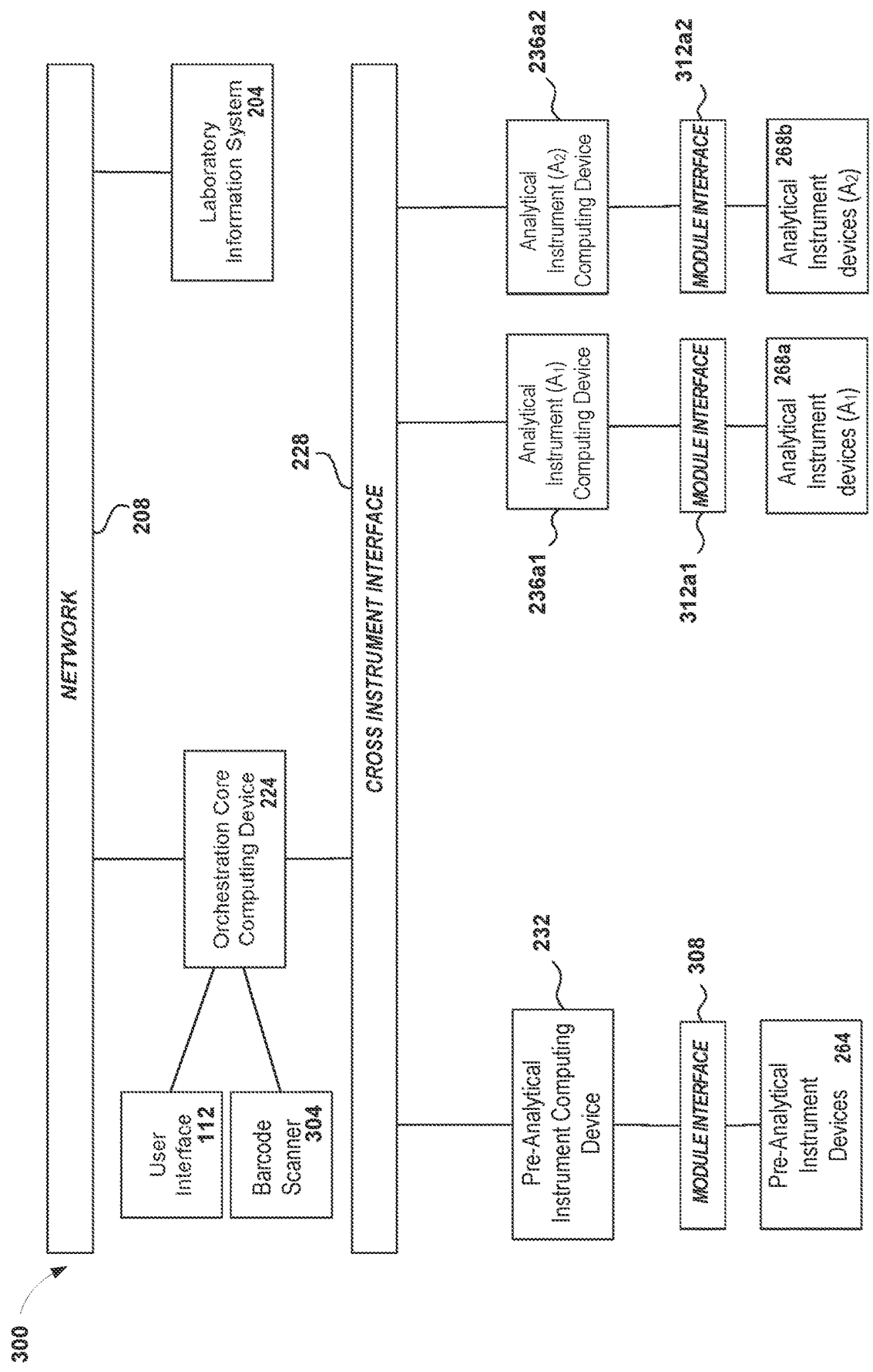
FIG. 3A is a block diagram of an orchestration core computing device architecture according to one embodiment described herein.

FIG. 3A depicts an orchestration core computing device architecture 300 that supports the analysis system 100, such as the analysis system 100 described with reference to FIG. 2A, according to an embodiment of the present disclosure. Architecture generally includes an orchestration core computing device 224 with a user interface, such as the user interface 112, to allow a user to communicate therewith. The orchestration core computing device 224 may include one or more code scanners 304 for reading sample identifiers (e.g., barcodes, QR codes) on sample containers or sample racks. The orchestration core computing device 224 is in communication with a pre-analytical instrument computer control device 232 of the pre-analytical instrument 104, and one or more analyzer computer control devices 236a1, 236a2 (illustrated here as two such control devices; one for each analyzer instrument) of the analytical instruments 108a, 108b. As shown, orchestration core computing device 224 is connected to a network 208, which is also connected to a laboratory information system 204 ("LIS"). The LIS 204 may be an existing generic or customized system associated with a diagnostic laboratory or medical facility that stores and maintains patient records, physician ordered assays, etc., among other things. The network 208 allows orchestration computer core computing device 224 to be communicatively coupled with the LIS 204 and share information therebetween. Orchestration core computing device 224 is also communicatively coupled to instrument control devices 232, 236a1, and 236a2 of instruments 104, 108a and 108b via a cross instrument interface 228. However, other interconnection mechanisms between the computer control devices 232, 236a1, and 236a2 and the orchestration core computing device 224 that allow the devices to share information with the system are contemplated.

Pre-analytical instrument computer control device 232, in addition to being connected to the cross instrument interface 228, is connected to a module interface 308 which is connected to the pre-analytical instrument devices 264 of system 100, allowing computer control device 232 to communicate with the pre-analytical instrument devices 264. The pre-analytical instrument computing device 232 includes an application stored on its memory which provides instructions to its processor involving control of the physical operations utilized in preparation and preprocessing of samples within system 100. In this regard, the application via the processor of pre-analytical instrument computer control device 232 helps control each instrument/device within pre-analytical instrument modules/devices 264.

Analyzer computer devices 236a1, 236a2 may also each include a processor and memory. Analyzer computing device 236a1, in addition to being connected to cross instrument interface 228, is connected to a module interface 312a1 which is connected to analyzer devices 268a of an analyzer instrument $A_1$, allowing analyzer computer device 236a1 to communicate therewith. Analyzer computing device 236a1 includes an application stored on its memory which provides instructions to its processor involving control of the physical operations utilized in analysis of a sample provided to the analyzer instrument $A_1$ via the system 100. In this regard, the analyzer computing device 236a1, via its processor, helps control each instrument/device within the analyzer instrument $A_1$. Analyzer computing device 236a2 is similarly configured for its respective analyzer instrument.

Thus, as shown in FIG. 3A, orchestration core computing device 224 receives information from multiple inputs and distributes the information as needed. This allows the system 100 to be fully integrated with one or more analyzer instruments and with an information sharing network that allows the system 100 to smartly perform preparation and preprocessing of multiple different samples contained in multiple different containers.

In another embodiment of architecture 300, pre-analytical instrument computer device 232 or analyzer computing devices 236a1, 236a2 may also act as the orchestration core computing device 224.

Each of the devices 232, 236a1, 236a2, and the orchestration core computing device 224 and the LIS 204 are at different nodes of the network 208 and capable of directly and indirectly communicating with one another. However, as depicted, orchestration core computing device 224 generally operates as a control interface between the LIS 204 and computing devices 232, 236a1, 236a2 of the analyzer instruments 108a, 108b and pre-analytical instruments 104. The computing devices 232, 236a1, 236a2 and the orchestration core computing device 224 and LIS within the network 208 may be interconnected using various protocols and systems. The network 208 may utilize standard communications protocols, such as Ethernet and Wi-Fi, and protocols that are proprietary to one or more companies, and various combinations of the foregoing. The communication between the laboratory information system 204 and the analysis system 100 may be via communication protocols, such as hypertext transfer protocol (HTTP) Although certain advantages are obtained when information is transmitted or received as noted above, the system described herein is not limited to any particular communication protocol.

Figure 3B:
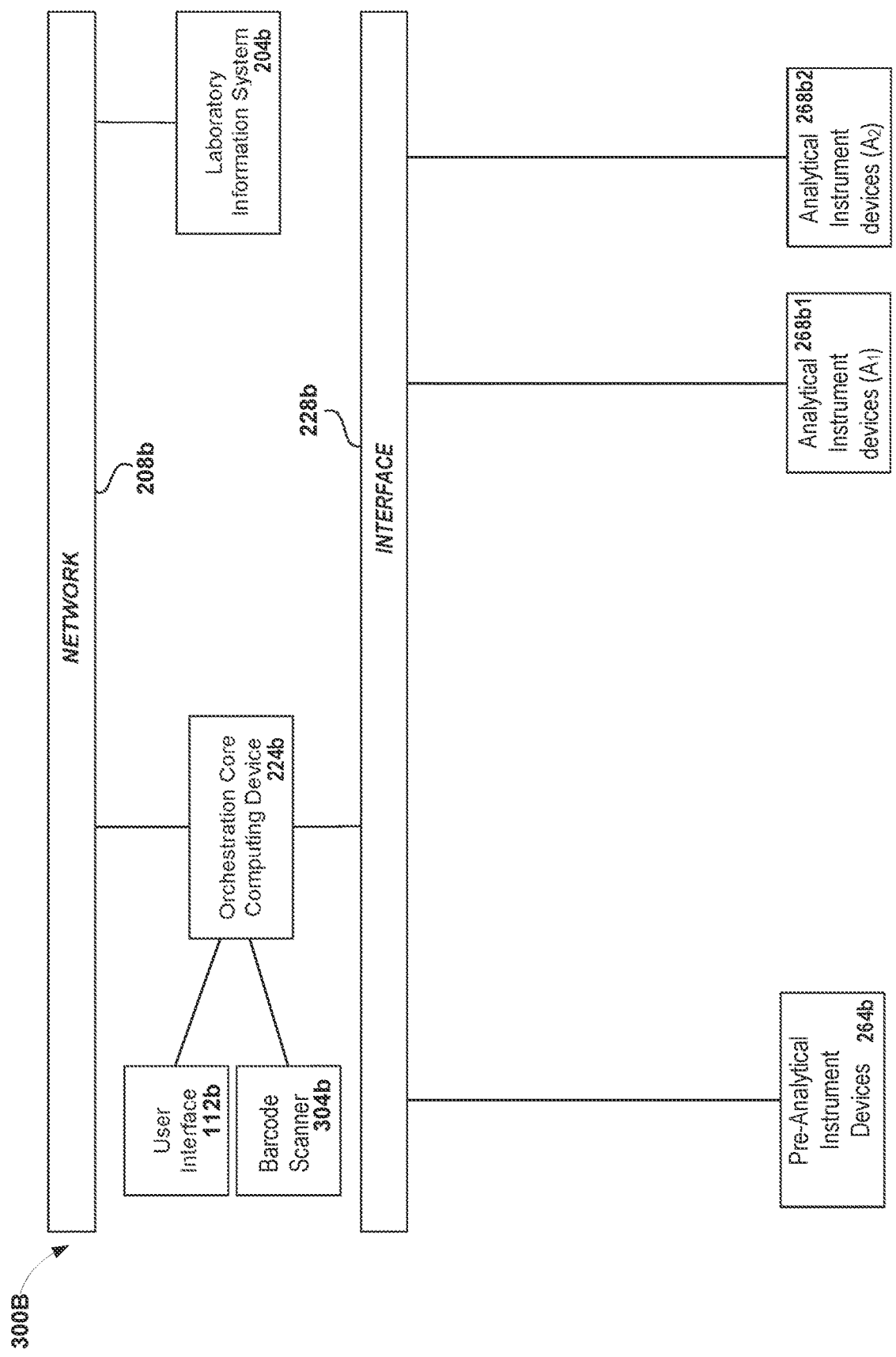
FIG. 3B is a block diagram of an orchestration core computing device architecture according to another embodiment described herein.

FIG. 3B is a block diagram of an orchestration core computing device architecture 300b according to the embodiment described with reference to FIG. 2B. The architecture 300b of the orchestration core computing device in FIG. 3B is similar to the architecture 300b of the orchestration core computing device described with reference to FIG. 3A. Because the analysis system 100b in FIG. 2B is a distributed system with the functions of the orchestration sub-applications 240b, 244b performed by the orchestration core computing device 224b, not the pre-analytical instrument 104b and analytical instrument 108b, the orchestration core computing device 224b communicates with and/or controls the pre-analytical instrument devices 264b and analytical instrument devices 268b1, 268b2 via an interface 228b, such as a cross instrument interface, an inter-device interface, or an intra-device interface.

Orchestration Core Application and Sub-Applications States

Figure 4:
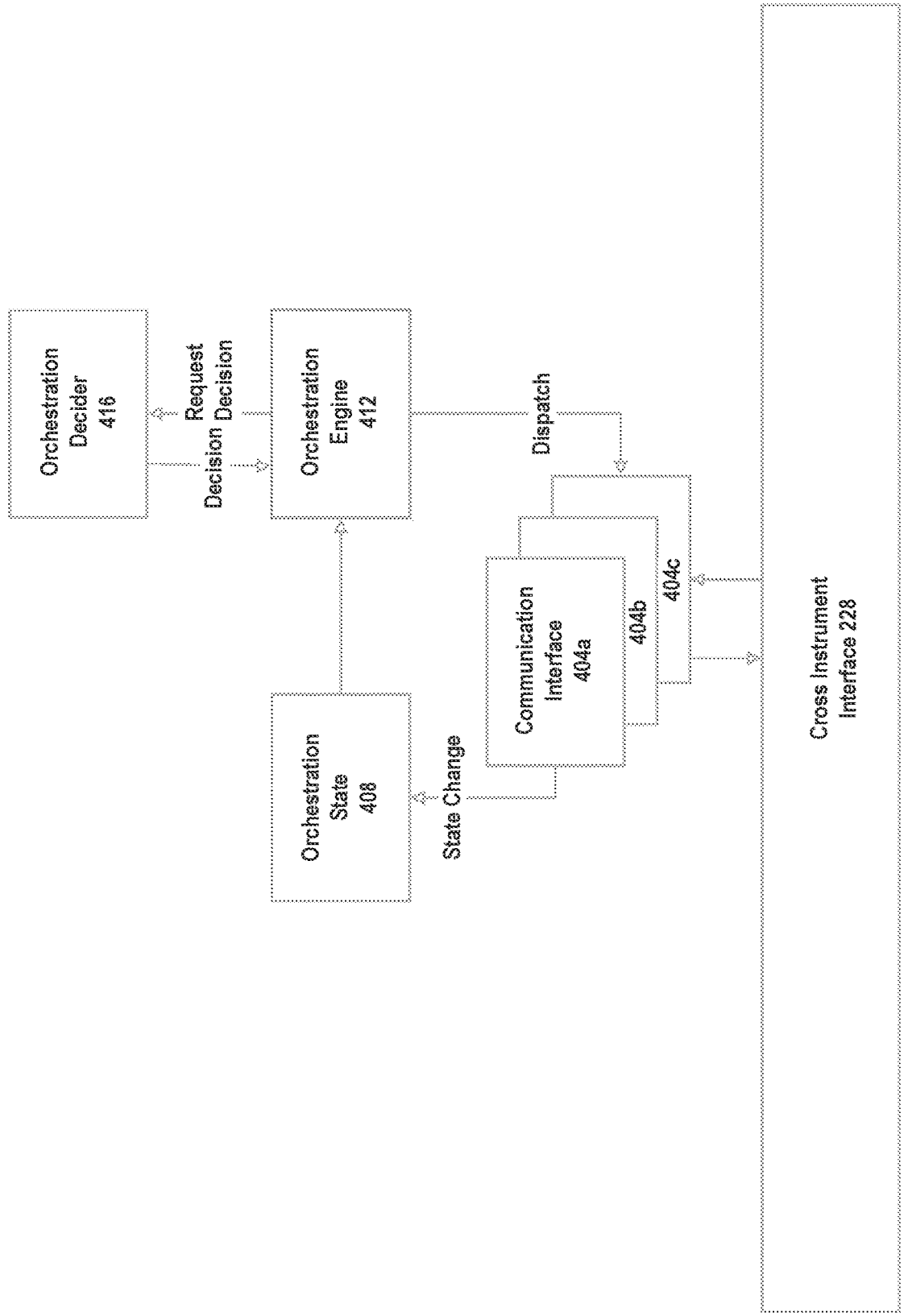
FIG. 4 is a block diagram of components of an orchestration core application according to one embodiment described herein.

FIG. 4 illustrates states of the orchestration core application or sub-applications. FIG. 4 illustrates multiple communication interfaces 404a-404c in bidirectional communication with the cross instrument interface 228. These communication interfaces each have a processor. These interfaces 404a-404c are processors through which the operations in each of the analytical 236a1, 236a2 and pre-analytical 232 systems are coordinated with the orchestration core computing device 224. Each of the communication interfaces 404a-404c is for either analyzer computing device 236a1, 236a2, or pre-analytical computer control device 232. In this regard, each computing device in 404a-404c contains one or more processors, memory and other components typically present in general purpose computing devices.

The communication interfaces 404a-404c forward information regarding state changes in the analytical and pre-analytical instruments to an orchestration state component 408 that is part of the pre-analytical instrument computing device 232 or one of the analyzer computing devices 236a1 or 236a2. The orchestration state component 408 communicates changes in state to the orchestration engine component 412 of the pre-analytical instrument computing device 232 or one of the analyzer computing devices 236a1 or 236a2. The orchestration engine component 412 is in bidirectional communication with the orchestration decider component 416 of the pre-analytical instrument computing device 232 or one of the analyzer computing devices 236a1 or 236a2. In response to requests from the orchestration engine component 412, the orchestration decider component 416 determines whether or not the orchestration engine component 412 is to dispatch instructions to the analytical and pre-analytical devices 108, 104.

Memory of each of the communication interfaces 404a-404c may store information accessible by the one or more processors, including instructions that may be executed by the one or more processors. The orchestration engine thread described above will execute on any available processor core in the communication interfaces 404a-404c. As noted above, the orchestration engine component 412 requests a decision from the orchestration decider component 416. If a decision is returned, the orchestration engine component 412 dispatches the action to the appropriate communication interface 404a-404c. When a communication interface 404a-404c receives a message involving state, it acquires the state from the orchestration engine component 412 and updates the orchestration state component 408 with its new state. The new orchestration state in the orchestration state component 408 then triggers the orchestration engine component 412 to run.

Memory includes data that may be retrieved, manipulated or stored by the processor. The memory may be of any non-transitory type capable of storing information accessible by the processor, such as a hard-drive, memory card, ROM, RAM, DVD, CD-ROM, write-capable, and read-only memories.

The instructions may be any set of instructions to be executed directly, such as machine code, or indirectly, such as scripts, by the one or more processors. In that regard, the terms "instructions," "application," "steps," and "programs" may be used interchangeably herein. The instructions may be stored in object code format for direct processing by a processor, or in any other computing device language including scripts or collections of independent source code modules that are interpreted on demand or compiled in advance. Functions, methods, and routines of the instructions are explained in more detail below.

Data may be retrieved, stored or modified by the one or more processors in accordance with the instructions. For instance, although the subject matter described herein is not limited by any particular data structure, the data may be stored in computer registers, in a relational database as a table having many different fields and records, or XML documents. The data may also be formatted in any computing device-readable format such as, but not limited to, binary values, ASCII or Unicode. Moreover, data may comprise any information sufficient to identify the relevant information, such as numbers, descriptive text, proprietary codes, pointers, references to data stored in other memories such as at other network locations, or information that is used by a function to calculate the relevant data.

The one or more processors implemented by each of communication interfaces 232, 236a1, and 236a2 may be any conventional processors, such as a commercially available CPU. Alternatively, the processors may be dedicated components such as an application specific integrated circuit ("ASIC") or other hardware-based processor.

In some embodiments, the processor or memory may actually comprise multiple processors and/or memories that may or may not be stored within the same physical housing. For example, the memory may be a hard drive or other storage media located in housings different from that of processor. Accordingly, references to a processor, computing device, or memory will be understood to include references to a collection of processors, computing devices, or memories that may or may not operate in parallel.

In the embodiment depicted in FIG. 2A, the analyzer computing devices 236a1, 236a2 and pre-analytical computing device 232 are located within their respective instruments. The location of the orchestration core computing device 224 is largely a matter of design choice. As shown in the orchestration core computing device 224 may also be in communication with a code scanner 304 and a user interface 112 of pre-analytical instrument 104 (FIG. 2A). The code scanner 304 is located within an input window 116 of pre-analytical instrument 104. In one embodiment, the user interface 112 is a touch screen device mounted to the outer shell of the pre-analytical instrument 104 (shown in FIG. 2A). However, it should be understood that user interface 112 may comprise a mobile device capable of wirelessly connecting to orchestration core computing device 224 wirelessly, such as via a Wi-Fi connection, for example. By way of example only, user interface 112 may be a mobile phone or a device such as a wireless-enabled PDA, a tablet PC, or a netbook that is capable of obtaining information via the network 208. In another example, orchestration device computing device 224 may be a desktop device located in a physical location remote from the analysis system 100.

Orchestration Core Application

As illustrated in FIG. 4, an orchestration core application 220 includes components for information flow such as communication interfaces 404a-404c, an orchestration decider component 416, an orchestration engine component 412, and an orchestration state component 408. The orchestration state component 408 receives and holds all information regarding the orchestration state (i.e., the states of sample processing and analysis for the system 100 that includes the pre-analytical and analytical systems). The orchestration decider component 416 implements an algorithm that determines next actions to be taken based on the orchestration state received from the orchestration state component 408. The communication interfaces 404a-404c are tasked with processing incoming information from analyzer instruments and pre-analytical instrument that is used to update the orchestration state.

The orchestration engine component 412 provides guarded access to the orchestration state, operates the orchestration decider component 416, and executes the decisions made by the orchestration decider component 416 in the form of instructions that are distributed to computing devices 232, 236a1, and 236a2. As previously mentioned, orchestration core application 220 is a state machine. Thus, state changes that occur during a decision making process invalidate the decision. The orchestration engine component 412 provides the guarded access to orchestration state component 408 while decisions are made so that the decisions made by orchestration core application 220 are atomic decisions (i.e. one decision at a time).

In one embodiment, in order to ensure such decisions are atomic, the orchestration engine component 412 runs on its own thread and is configured to implement one or more strategies for preventing state updates during a decision making process. In other embodiments, the thread is not configurable on the fly. For example, in one embodiment, the orchestration engine component 412 is configured to lock the orchestration state while a copy of the orchestration state is made. Such copy of the orchestration state is used in the decision making process. This allows the lock on the orchestration state to be applied for a short period of time limiting the opportunity for a race condition Race conditions may occur when multiple pieces of state data change during execution of a decision. For example at the start of the decision there is one batch and thirty patient samples, and at the end of decisions there are two batches and sixty samples. Both of these states are consistent. If the orchestration state is not controlled by the orchestration engine component 412 could see the inconsistent state of one batch and sixty samples, and therefore make an "invalidate" decision.

In another embodiment, the orchestration engine component 412 may be configured to first determine what action to perform, and then execute the action. Additionally, the orchestration engine component 412 may be configured to apply a lock to the orchestration state during the decision making process. This may also allow the lock to be applied for a short period of time provided the decision regarding which action to perform is quick. Delayed decisions may delay processing and a delayed decision may stop the state from being updated.

In a further embodiment, all state changes are automatically entered into a queue. The orchestration engine component 412 may be configured to wake from a waiting condition, such as exiting a waiting or sleep state, and process each of the changes in the queue. Once the queue is empty, the orchestration engine component 412 may be configured to then run the orchestration decider component 416 and execute the decisions.

In another embodiment, the orchestration core application 220, which may be implemented by the orchestration core computing device 224, is configured to apply a lock over the orchestration engine component 412 and orchestration state component 408. The lock is freed if the orchestration engine component 412 is in a waiting condition, which indicates all activities associated with the locked-down state are completed. In this embodiment the lock is held for a longer time and may prevent other threads from executing if the orchestration engine component 412 is busy. Because of the longer lock, a race condition is more likely.

Orchestration Sub-Application System

Figure 5A:
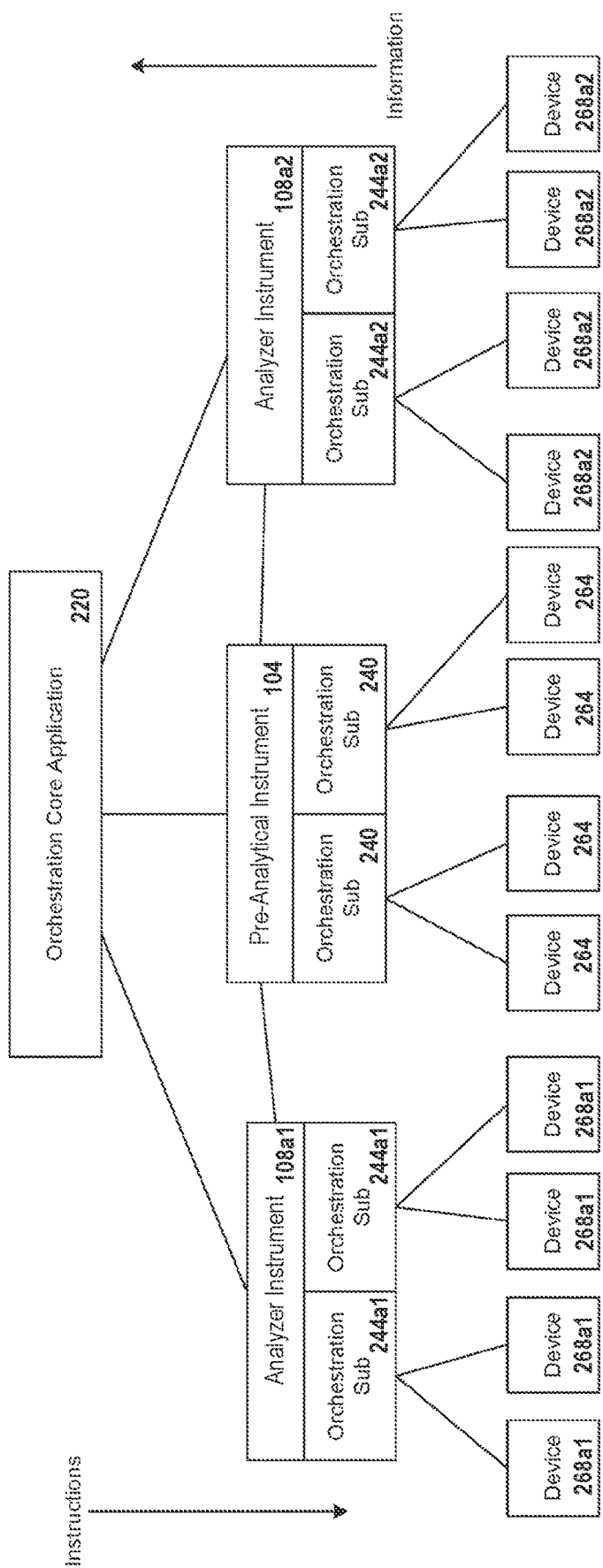
FIG. 5A is a block diagram of an orchestration core application and orchestration sub-applications according to one embodiment described herein.

As depicted in FIG. 5A, analyzer instruments 108a1 and 108a2 and pre-analytical instrument 104 include orchestration sub-applications 240, 244a1, 244a2. These applications 240, 244a1, and 244a2 are stored on the respective memories of the computing devices 232, 236a1, and 236a2 and provide instructions to their respective processors involving the coordination and control of the hardware devices within units 104, 108a1 and 108a2, such as the hardware devices described above. The orchestration sub-systems 240, 244a1, and 244a2 are the communication link between the orchestration core application 220 and individual components/subsystems/hardware within instruments 104, 108a1 and 108a2. In this regard, sub-applications 240, 244a1, and 244a2 assist in executing instructions provided by orchestration core application 220 and allow for the modularity of each instrument 104, 108a1 and 108a2. Thus, as shown, instructions flow from the orchestration core application 220 to the individual devices of the instruments 104, 108a1 and 108a2. Such general instructions translate into targeted actions by discrete devices through programming by delegation of authority as the instructions are communicated in a direction toward the hardware devices. For example, when the pre-analytical instrument 104 receives a rack of samples, one or more of the orchestration sub-applications 240 issue specific instructions to specific devices 264 to accomplish the tasks necessary in support of receiving the rack of samples into the pre-analytical instrument 104. In this regard, information flows from the individual devices 264 to the orchestration core application 220. Such information may include operational states of the devices 264, current levels of consumables and locations of particular samples. This pyramid structure allows orchestration core application 220 to focus on high-level decisions and information gathering.

The orchestration sub-applications 240, 244a1, and 244a2 may be configured similarly to the orchestration core application 220 to coordinate activities amongst the various devices within each unit 104, 108a1, 108a2 and also across the units, 104, 108a1, 108a2. For example, a conveyor manager sub-application of pre-analytical instrument 104 and a robotic arm manager sub-application of the second analyzer instrument 108a2 may coordinate the availability and operation of a respective conveyor and robotic arm so as to hand-off sample containers from the conveyor of the pre-analytical instrument 104 to the robotic arm of the analyzer instrument 108a2.

In addition, the sub-applications 240, 244a1, 244a2 may be state machines that operate on their own threads. For example, pre-analytical instrument 104 may have a rack manager sub-application that is a state machine operating on its own thread. The rack manager sub-application may be responsible for coordinating activities that move a rack of samples throughout the pre-analytical instrument 104. For example, rack manager sub-application may hold rack objects and make decisions based upon a rack state value assigned to the object, which may be a single enumeration that indicates where the rack is and what operation is being performed on it. Such decisions may include which rack of samples to move and where it will be moved to. In addition, the rack manager sub-application coordinates the hand-off of a rack with other components or stations within pre-analytical instrument 104, such as a sample conversion station or a rack elevator.

However, because the rack manager sub-application is a state machine, state changes that occur during a decision making process invalidate the decision. In order to ensure such decisions are atomic, the rack manager sub-application is configured to implement one or more strategies for preventing state updates during a decision making process. For example, in one embodiment, rack manager sub-application may be configured to apply a lock to the rack states while a copy of the rack states is made. Such copy would be used in the decision making process. This would allow the lock to be applied for a short period of time limiting the opportunity for a race condition.

Figure 5B:
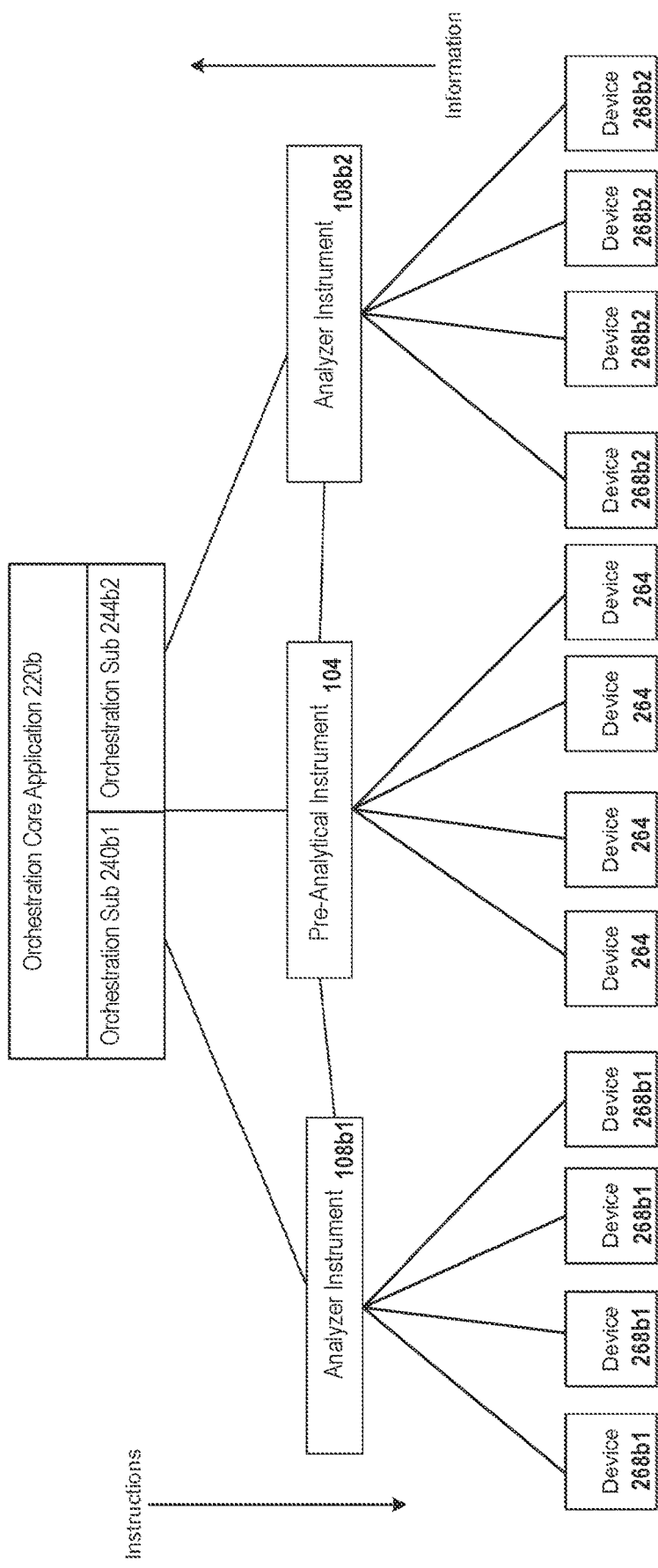
FIG. 5B is a block diagram of an orchestration core application and orchestration sub-applications according to another embodiment described herein.

FIG. 5B is a block diagram of an orchestration core application and orchestration sub-applications of the centralized analysis system described with reference to FIGS. 2B and 3B. As depicted in FIG. 5B, the orchestration sub-systems 240b, 244b1, and 244b2 are the communication link between the orchestration core application 220b and individual components/subsystems/hardware within instruments 104b, 108b1 and 108b2. The orchestration sub-applications 240b, 244b1, and 244b2 may be configured similarly to the orchestration core application 220b to coordinate activities amongst the various devices within each unit 104b, 108b1, 108b2 and also across the units, 104b, 108b1, 108b2. The sub-applications 240b, 244b1, 244b2 may be state machines that operate on their own threads. The core application 220b may be a state machine that operates on its own thread.

Multi-Layer Orchestration Core Application Architecture

Figure 6:
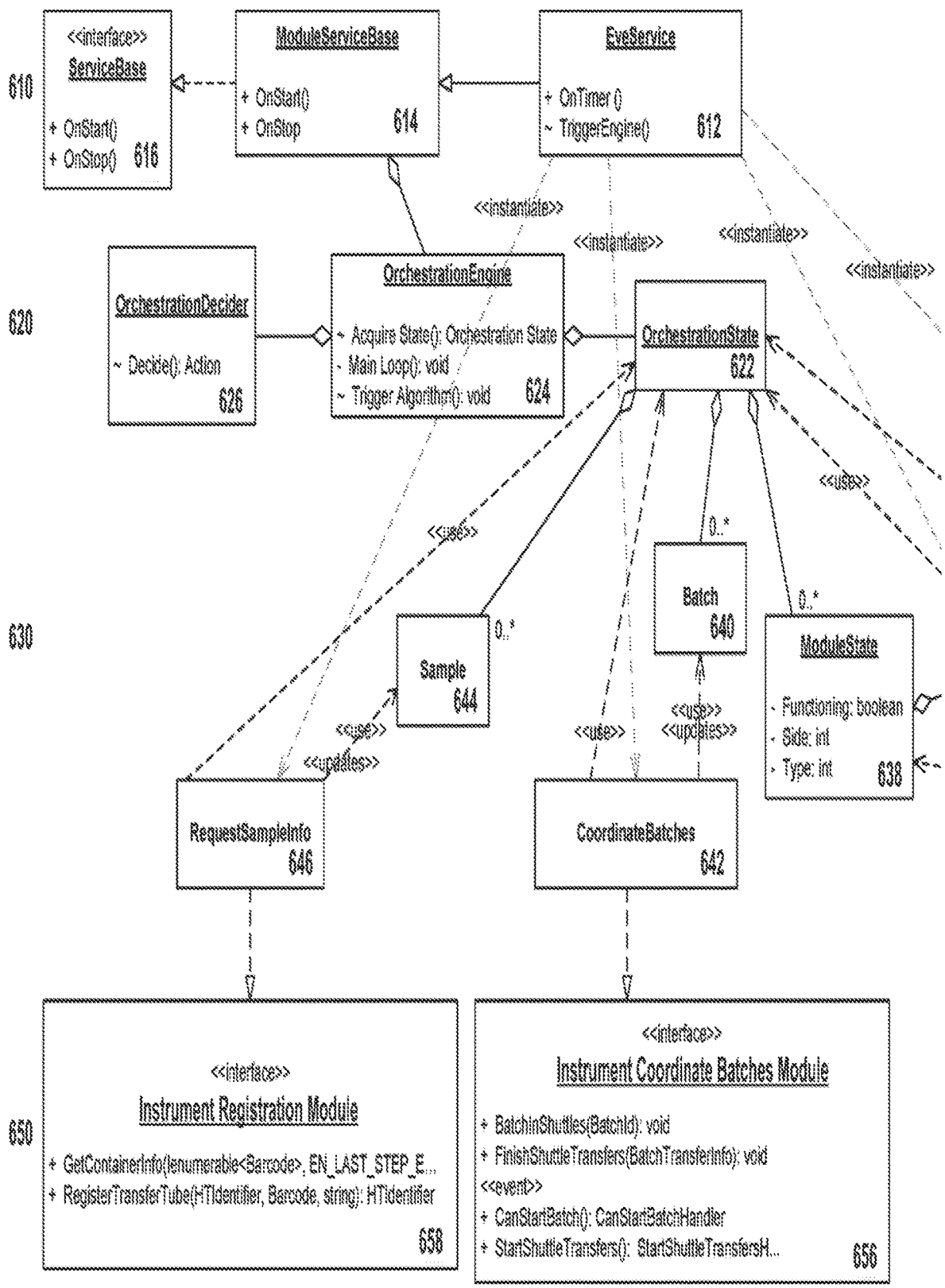
FIG. 6 illustrates one embodiment of an orchestration core application described herein.
Figure 6:
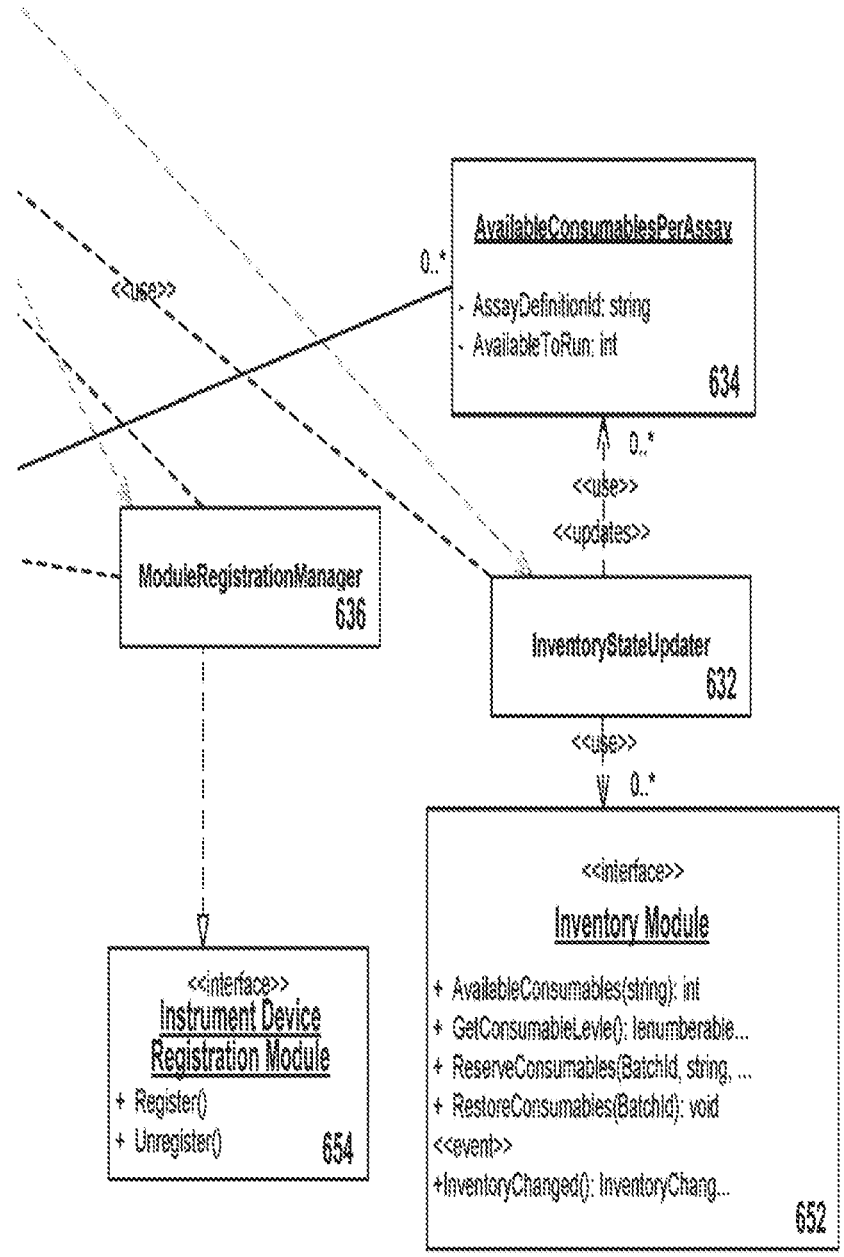

FIG. 6 illustrates an architecture for the orchestration core application 220 which, as illustrated, has a multi-instrument service layer 610, an orchestration layer 620, and an instrument module layer 630. Each layer is assembled from a plurality of system user objects, each encapsulating a separate user operational category. The plurality of system user objects advantageously include (1) a service level object 610 layer that includes the module service base module 614 for the system illustrated in FIG. 6. The service level object layer 610 is part of the orchestration control application service module 612 which is in communication with the orchestration layer 620, the instrument module control layer 630, and modules in the instruments module layer 650. The orchestration control application service module 612 is in communication with the module that requests sample information 646, the module that coordinates batches 642 the module that manages module registration 636 and the module that updates inventory status 632. The orchestration control application service module 612 also communicates with other modules in its layer (i.e. the module service base module 614 and, through the module service base module 614, the service base module 616).

In one embodiment, the orchestration engine module (or component) 624 communicates with the module service base module 614 that also receives instructions from the orchestration control application service module 612. The orchestration engine module 624 acquires orchestration states from the orchestration state module 622. The orchestration state module 622 receives state information from every module in the layer 630 and, indirectly, every module in the layer 650. These modules are the inventory state updater module 632, the available consumables per assay module 634, the module registration manager 636, the module state module 638, the batch module 540, the coordinate batches module 642, the sample module 644 and the request sample information module 646. In response to requests from the orchestration engine module 624, the orchestration decider module 626 determines whether or not the orchestration engine module 624 is to dispatch instructions to other modules.

The request sample information module 646 communicates with the instrument registration module 658 to provide instructions and obtain information regarding the registration and tracking of individual samples in the instrument. In one embodiment the sample information is obtained by reading the sample code on the sample container received by the instrument. The sample code on the transfer container is also registered to identify and track the transfer containers in the instrument. Note that the orchestration control application service module 612 initiates the sample information request from the request sample module 646 which causes the instrument registration module 658 to obtain the information about the sample containers and transfer containers. Once the sample information is obtained, the sample information in the sample information module 644 is updated. The updated sample information is communicated to the orchestration state module 622.

Layer 630 also has a module 642 that coordinates batches by communicating with the instrument coordinate batches module 656 in the instrument. Through the interface with the coordinate batch module in layer 630, the instrument coordinate batches module 656 populates shuttles with samples designated by the orchestration control application service module 612 to be in the same batch. The coordinate batch module 642 also provides instructions to the instrument coordinate batches module 656 to start the batch handler apparatus in the instrument coordinate batches module 656 and for the instrument coordinate batches module 656 to start shuttle transfers. The coordinate batch module 642 communicates with both the orchestration state module 622 and the batch module 640 (which in turn communicate with the orchestration state module 622).

Layer 630 also has a module 640 that communicates the module state to the orchestration state module 622. The module state module 638 acquires information from the module registration manager 636 which receives instructions and direction from the orchestration control application service module 612 in layer 610. The module registration manager 636 also communicates information to the orchestration state module 622. Based on instructions from the orchestration control application service module 612, the module registration manager 636 communicates with the instrument device registration module 654.

As noted above, the layer 630 has a module 632 that updates the inventory state. The inventory state module 632 receives instantiation instructions from the orchestration control application service module 612 and updates the orchestration state module 622 with any state updates. The inventory state update module 632 controls the inventory module 652 in the pre-analytical instrument to obtain a variety of information about the state of consumables in the instrument. That information includes the inventory information on the available consumables; retrieving consumables as required; reserving consumables; restoring consumables; changing the inventory.

In another embodiment, a rack manager sub-application may be configured to first determine actions to perform, and then execute such actions. Additionally, the rack manager-sub application may be configured to apply a lock to the rack states during the decision making process. This may also allow the lock to be applied for a short period of time provided the decision regarding which action to perform quickly made.

In a further embodiment, all rack state changes are automatically entered into a queue. The rack manager sub-application may be configured to wake from a waiting condition and process each of the changes in the queue. Once the queue is empty, the rack manager sub-application may be configured to execute the decisions.

In an even further embodiment, the rack manager sub-application may be configured to apply a lock over the rack manager sub-application. The lock is freed if the rack manager sub-application is in a waiting condition, which indicates all activities associated with the locked-down rack states are completed.

Instrument and Assay States

In one embodiment, the instruments are provided with defined states. For example, the instrument states may be defined as illustrated in Table 1.

TABLE 1

State Definitions

| STATE | DESCRIPTION |
|---|---|
| Offline Busy | The instrument is not available for general scheduling or concurrent activity. It is executing a single offline activity. |
| Offline Idle | The instrument is not available for general scheduling or concurrent activity. |
| Online Busy | The instrument is online and performing one or more concurrent procedures. |
| Online Idle | The instrument is available for general scheduling and concurrent activity. |
| Paused Idle | An online instrument is paused while idle. No new procedures may be initiated while paused. |
| Paused Busy | An online instrument that is performing one or more concurrent activities is paused between steps. Execution of those activities continues after the instrument is resumed. No new procedures may be initiated during pause. |
| Power Off | The instrument is powered down. |

Figure 7:
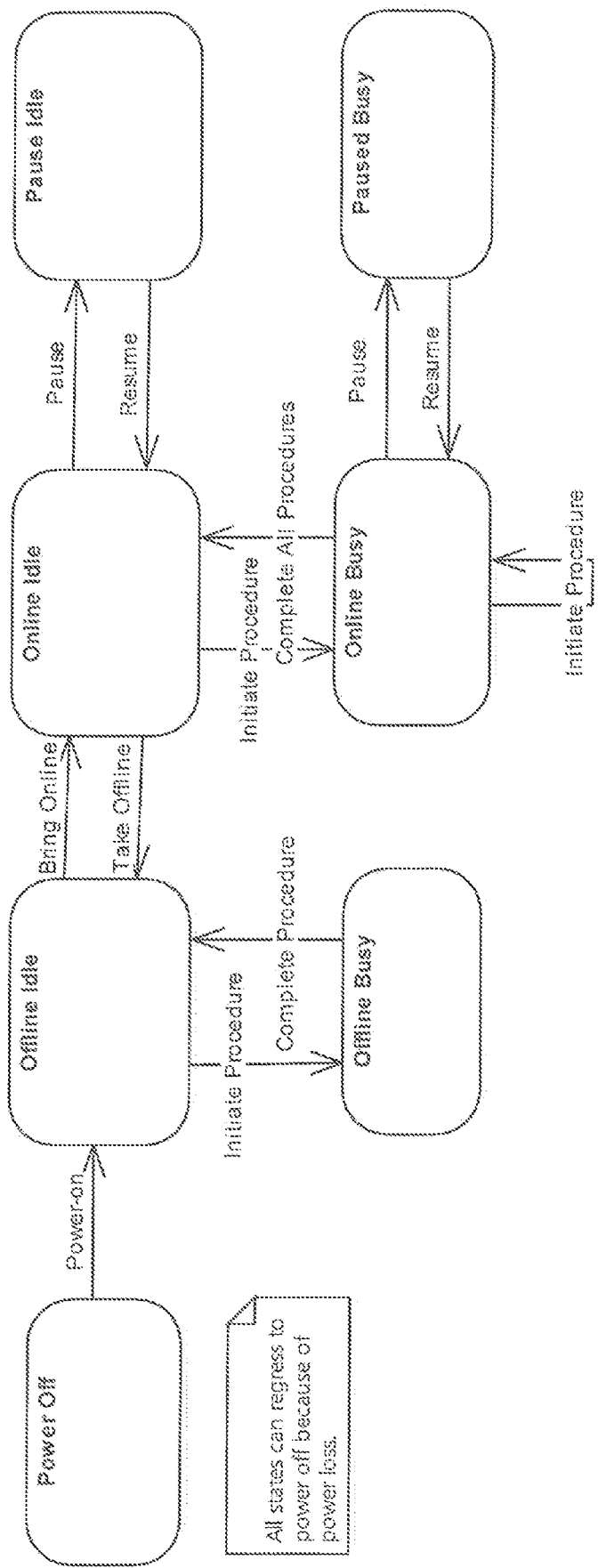
FIG. 7 is a block diagram illustrating various instrument states for an analysis system.
Figure 8:
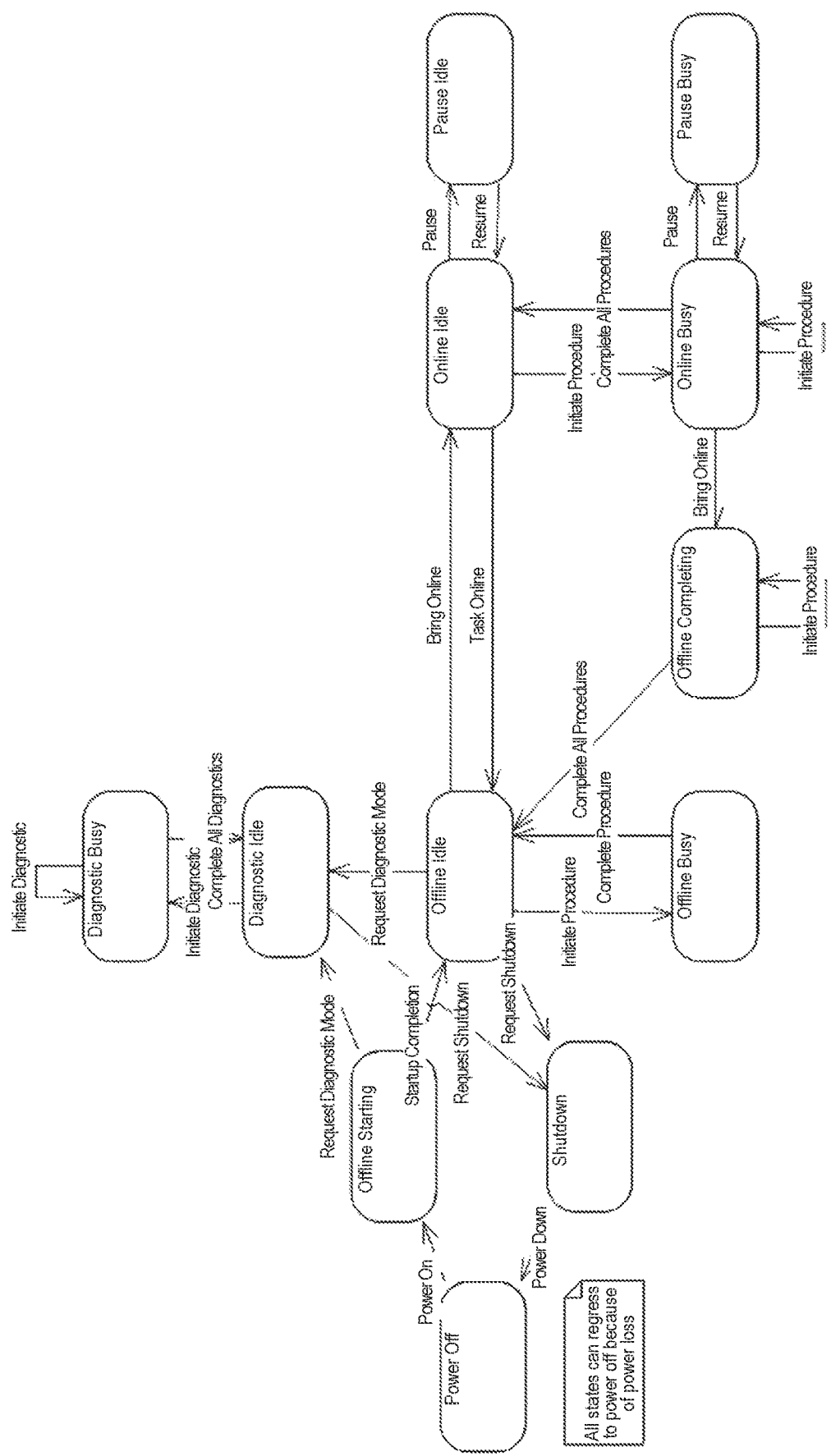
FIG. 8 is a block diagram illustrating various instrument states for an analysis system.

Referring to FIG. 7 and FIG. 8, the commands that will change one state to another are illustrated. For example, when an instrument is in the power off state, a command to power on will change the state to "offline idle." The offline idle state may either change to "offline busy" when an offline procedure (e.g. instrument service; software update, etc.) is executing, in which case the offline idle state is maintained until after the offline procedure is completed. If there is no offline procedure preventing the state from changing from offline idle to online idle, a command to bring the instrument online with change the state to online idle. In the online idle state, the instrument may be instructed to initiate a procedure. Once completed, the instrument is returned to the online idle state. If the instrument is paused during execution (paused busy), no new procedures may be initiated until the state is returned to online busy and the procedure is completed. When the instrument is in the online idle state, it will remain available to receive commands for further activity unless it enters the pause idle state, in which case no new procedures may be initiated or an instruction is received to take the instrument offline.

The system also has defined assay states. In one embodiment, the assay may have one of the states set forth in Table 2 below.

TABLE 2

Assay State Definitions

| STATE | DESCRIPTION |
|---|---|
| Not Allowed | The assay may not be performed on this machine because of region rules or lab qualifications. |
| Unqualified | The assay is allowed to be performed on this machine, but is not qualified for patient samples. |
| Qualified | Assay had been qualified for use on this machine. Patient sample may be performed on this assay. |
| New Version Available | The machine is qualified to perform version of the assay, but a new official version has been released. The lab has yet to qualify this version of the assay. The old version is still performed for all new batches of the assay. |

Figure 9:
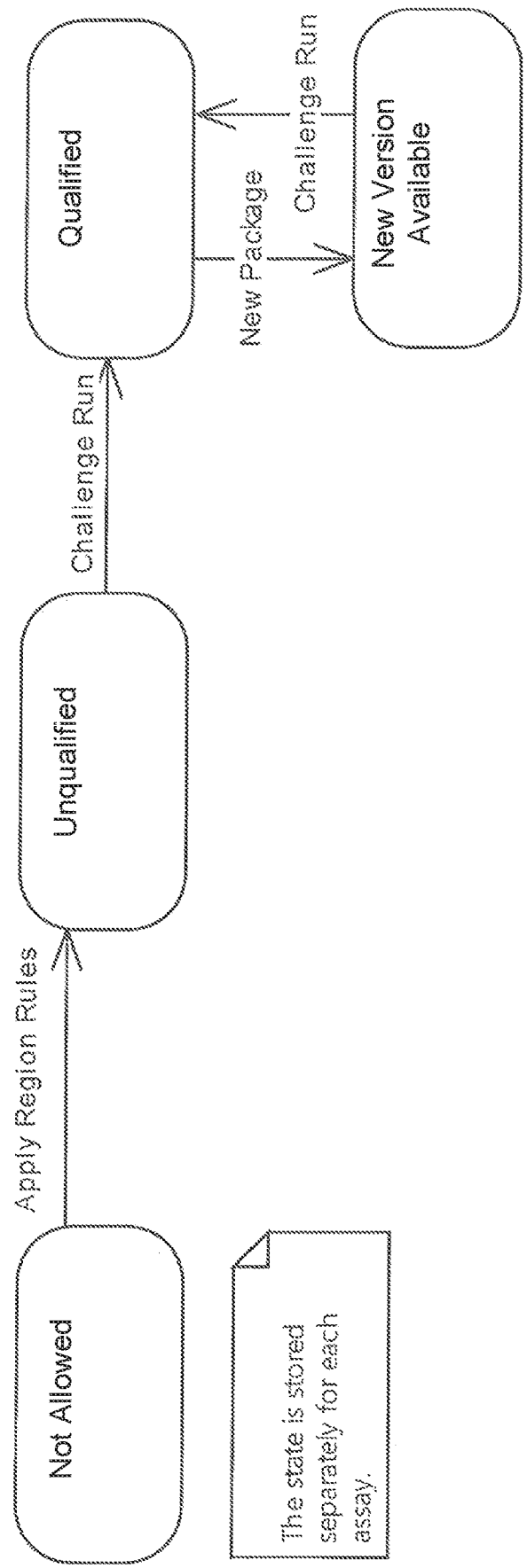
FIG. 9 is a block diagram that illustrates exemplary assay states for an analysis system.

FIG. 9 illustrates how the state is stored for a particular assay. If the assay state is "not allowed" then region rules for the assay are applied, in which case the assay is provided with an "unqualified" state that will allow the assay to be performed but the assay results will not be patient qualified. To obtain qualification, the performed is challenged. If the state is qualified, but a new version of the assay has been released, the older version of the assay is performed until the new version is qualified.

Determining an Assays or Assay Steps Order

Figure 10:
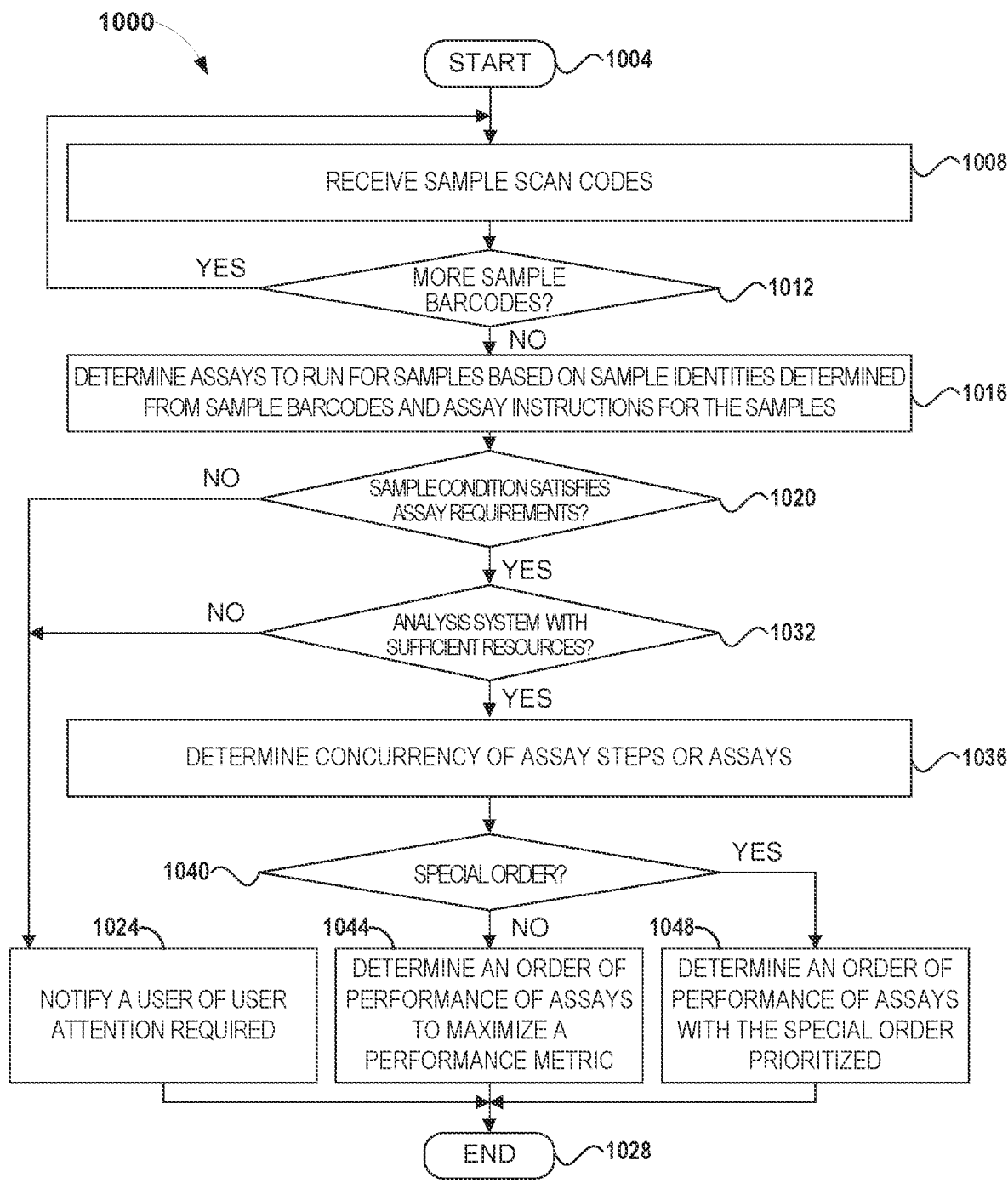
FIG. 10 is a flow diagram of one exemplary method of determining an order of performance of assays or assay steps for samples to maximize performance in an analysis system.

The orchestration core application 220 may determine an order of performance of assays or assay steps based on the samples received, the assays ordered, and availabilities of resources 248, 252. FIG. 10 is a block diagram of a non-limiting exemplary method 1000 of determining an order of performance of assays or assay steps for samples to maximize performance. In one embodiment, the orchestration core application 220 may implement the method 1000 or a part of the method 1000. After beginning at a block 1004, the method 1000 receives scanned sample codes at a block 1008. For example, after a rack of samples in containers arrives at the input window 116 of the analysis system 100, the code scanner 304 of the analysis system 100 may scan sample identifiers affixed to the containers of samples, such as barcodes and two dimensional codes. The method 1000 may receive scanned sample codes as they are scanned by the scanner 304. At a decision block 1012, if the scanner 304 scans and receives additional sample codes, the method 1000 may return to the block 1008 to receive more sample codes. The additional sample codes may be from the same rack of samples or another rack of samples received by the analysis system 100.

At the decision block 1012, if no additional sample code is scanned and received, the method 1000 may proceed to a block 1016, where the method 1000 determines assays to perform for the samples received and scanned. For example, the method 1000 may receive assay instructions for the samples received and scanned from a laboratory information system 204 or a hospital information system. The method 1000 may determine assays to perform for the samples based on the sample identities determined from sample codes and the assay instructions. For example, a doctor may order three tests A, B, and C for a patient, and the container containing the patient's sample may have a sample code 123456 affixed to it. After the method 1000 receives the sample code 123456, the method 1000 may determine the identity of the sample (i.e., the patient's sample) and determine that the doctor has ordered or instructed three assays for the patient.

The method 1000 proceeds to a decision block 1020, where the method 1000 determines whether the condition of each sample satisfies the requirements of the one or more assays ordered for the sample. The condition of the sample may be the sample volume, the sample age, the sample quality (e.g., sample opacity). For example, the three assays A, B, and C ordered by the doctor for the patient require 1 ml, 5 ml, and 10 ml respectively. However, the volume of the patient's sample, as determined by the pre-analytical instrument 104, may only be 15 ml. Thus, the volume of the patient's sample does not satisfy the total requirements of the three assays ordered because at the volume of the patient's sample is sufficient for two assays only. If the sample does not satisfy the requirements of the one or more assays ordered, the method 1000 proceeds to a block 1024, where the method 1000 notifies a user that the sample condition does not satisfy the requirements of the ordered assays. For example, the orchestration core application 220 may display an error message using the user interface 112 of the analysis system 100. The method 1000 then ends at a block 1028.

In some implementations, the assay instruction for a sample may include a priority of the assays to be performed. The method 1000 may determine the assays that should be performed on a sample, even though the condition of the sample does not satisfy the requirements of all the assays ordered for the sample. For example, the assay instruction of the patient's sample may indicate that the results of the assays A and B may only be interpreted together. The assay instruction may also indicate that assay A is more important than assay C. Thus, the method 1000 may proceed from block 1020 to perform assays A and B, and notify the user that assay C will not be performed. In some implementations, the method 1000 may display the possible assays that may be performed for the sample and request user input regarding the assays that should be performed.

At the decision block 1020, if the sample condition satisfies the requirements of the assays ordered, the method 1000 proceeds to a decision block 1032, where the method 1000 determines whether the analysis system 100, including the pre-analytical instrument 104 and analyzer instrument 108, has sufficient resources to perform all the assays ordered. If the analysis system 100 does not contain sufficient resources, the method 1000 proceeds to the block 1024, where the user is notified that the analysis system 100 does not include sufficient resources to perform the ordered assays. The method 1000 then proceeds to the block 1028, where the method 1000 ends. For example, the pre-analytical instrument 104 may need to pipette the patient's sample from the sample container into three smaller containers. However, the pre-analytical instrument 104 may be out of pipette tips or may only have two smaller containers. The method 1000 may notify the user, via the user interface 112, that the user needs to stock the pre-analytical instrument 104 with more pipette tips and containers.

Table 3 illustrates exemplary resources of the analysis system 100 that may require exclusive access such that each resource may only be used for the preparation or analysis of one sample or one batch of samples. Some of these resources may be initiated by the analysis system 100 automatically. Some of these resources may require specific user initiations or user actions, possibly after the analysis system 100 provides a user with options for the user to choose. For example, a user may initiate the emptying of a waste container of the analysis system 100. As another example, during daily maintenance, the analysis system 100 may pause until a user acknowledges that the extraction area has been cleaned. Table 4 illustrates exemplary additional resources of the analysis system 100.

TABLE 3

Resources of the Analysis System that May Require Exclusive Access

| Group | Name | Initiation |
|---|---|---|
| Maintenance | Daily | User schedule or request |
| Sample | Conversion | Rack in hotel |
| Sample | Pass-Through | Rack in hotel |
| Sample | HPV Sample Batch | Assembled batch |
| State Change | Software update | User scheduled |
| State Change | Pause Dory | User request |
| Racks | Load Sample Racks | Rack in I/O bay |
| Racks | Unload completed racks | User request |
| Consumables | Stock Dory consumable drawer | User request |
| Consumables | Empty Roz waste | User request |
| Interventions | Stuck Tubes in shuttle | Consumable failure |

TABLE 4

Resources of the Analysis System

| Resource Name | Module | Side | Concurrency | Constituent Devices | Constituent Resource |
|---|---|---|---|---|---|
| Light bar | Analysis system | NA | Shared | Light bar | |
| Console | Orchestration core application | NA | Shared | All-in-one display | |
| Inventory robot 1 | Pre-analytical instrument | Any analysis instrument | Shared | Inventory robot | |
| Operator | NA | NA | Shared | A logged in lab tech | |
| Deck | Analysis instrument | Any analysis instrument | Reserved | Conveyor, Gantry robot, Gripper, Sealer, Shaker 1 & 2, Shuttle transporter, Tube restraint | |
| Reader 1 | Analysis instrument | Any analysis instrument | Reserved | Reader 1 | |
| Consumable drawer 1 | Analysis instrument | Any analysis instrument | Reserved | Consumable drawer, extractor | |

TABLE 4-continued

Resources of the Analysis System

| Resource Name | Module | Side | Concurrency | Constituent Devices | Constituent Resource |
|---|---|---|---|---|---|
| Consumable drawer 2 | Analysis instrument | Any analysis instrument | Reserved | Consumable drawer, extractor | |
| Tip drawer | Analysis instrument | Any analysis instrument | Reserved | Tip drawer | |
| Trough 1 | Analysis instrument | Any analysis instrument | Reserved | none | |
| Top cabin | Analysis instrument | Any analysis instrument | Reserved | Top cabin doors | Deck, Consumable Drawer 1-6, Tip Drawer, Trough 1-2 |
| Waste | Analysis instrument | Any analysis instrument | Reserved | Liquid, solid and plate waste | |
| Bottom cabin | Analysis instrument | Any analysis instrument | Reserved | Bottom cabin doors | Waste |

In one implementation, the method 1000 may determine the combination of assays that may be performed given the shortage of system resources and let the user determine the assays that should be performed. In another implementation, the assay instructions may include assay and sample priorities such that the method 1000 may notify the user of the lack of system resources and proceed from the decision block 1032 to perform the assays based on the assay and sample priorities.

At the decision block 1032, if the analysis system 100 contains sufficient resources, the method 1000 proceeds to a block 1036, where the assay steps or the assays that the analysis system 100 may perform concurrently are determined. For example, if assays A and B ordered for the patient requires heating at 65° C. and 95° C. respectively, and if the analyzer instrument 108 contains only one heat plate for heating samples, then these two steps may not be performed concurrently. However, if the analyzer instrument 108 contains two or more heat plates, then these two assay steps may be performed concurrently.

The method 1000 proceeds to a decision block 1040 to determine whether the assay instructions include any special instructions. For example, a special instruction may state that the assay instruction for a particular patient is a rush instruction and has the highest priority. As another example, a special instruction may indicate that either two assays are both performed or neither is performed (possibly because the results of the assays for a patient need to be interpreted together). If there is no special instruction, the method 1000 proceeds to a block 1044 to determine an order of performance to maximize a performance metric. The performance metric may be based on one or more factors such as the time duration for performing all the assays, the energy used for performing all the assays, and quality or accuracy of assay results. The order of performance may be affected by scheduled events. For example, scheduled events may be daily maintenance, scheduled firmware or software updates, scheduled hardware upgrade, and scheduled power outage. The order of performance may be affected by the physical or logical configurations of the components of the analysis system 100. For example, the order of performance may be affected by the physical or local configurations of the pre-analytical instrument 104, analytical instrument 108, and electronic instruments 264, 268. The order of performance may be affected by the types of sample containers or other identifying elements of the sample. For example, the container containing a sample received may not be preferred for a type of assay ordered for the sample. The order of performance may include a step of transferring the sample from the sample container received to a more appropriate sample container. The method 1000 then ends at the block 1028.

At the decision block 1040, if the assay instructions include a special instruction, the method 1000 may proceed to a block 1048 to determine an order of performance of the assays to be performed with the special instruction prioritized while maximizing the performance metric. For example, if an assay order for a patient is a rush order, the method 1000 may determine an order of performance that maximizes the performance of the assays other than those of the assays for the rush instruction. In some embodiments, the performance of the assays is minimized unless all rush instructions are performed first. The method 1000 then ends at the block 1028.

Example Order Determination

Figure 11:
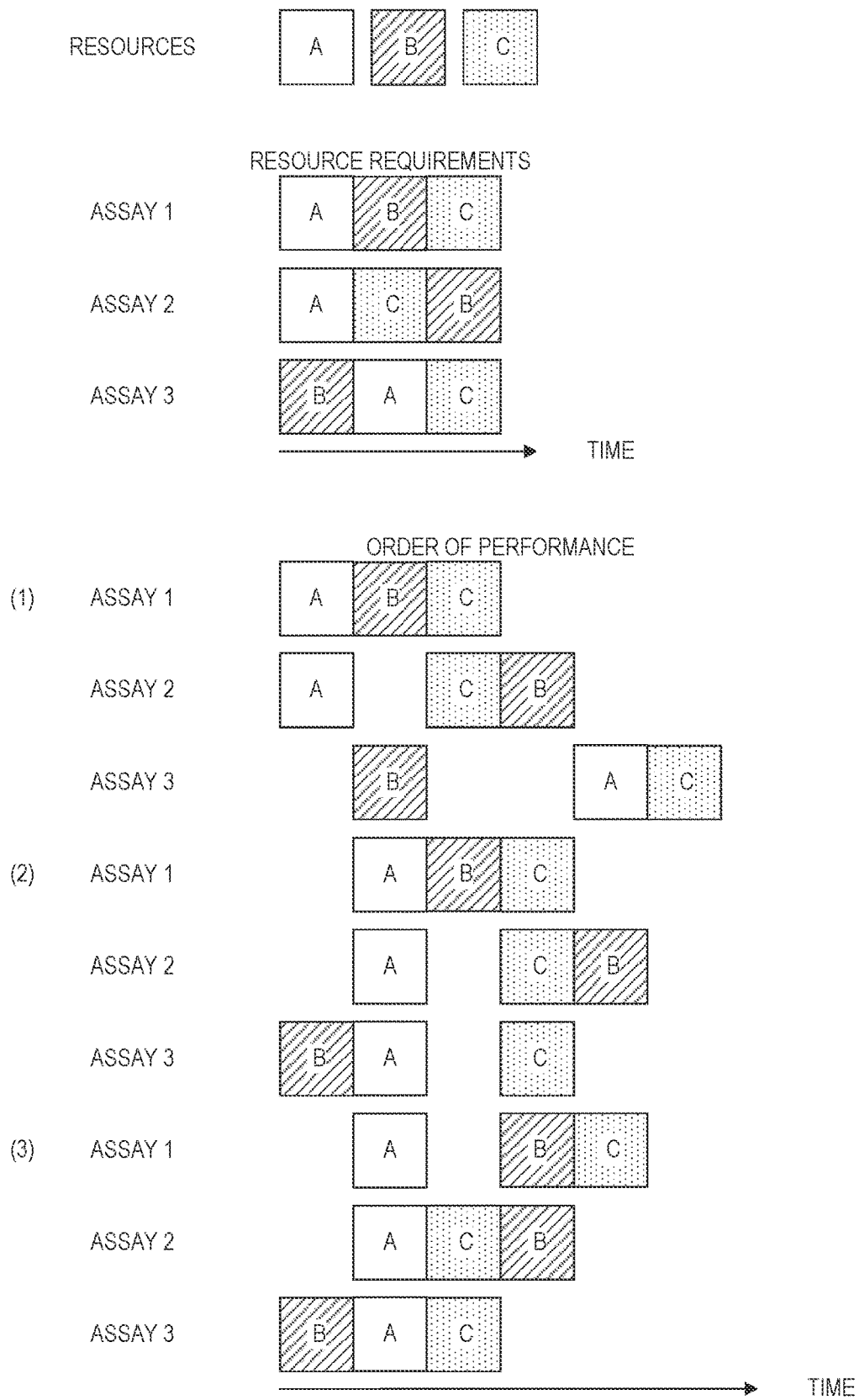
FIG. 11 is a block diagram of one example of determining an order of performance of assay steps for samples to maximize performance in an analysis system.

FIG. 11 is a schematic illustration of a non-limiting example of determining an order of performance of assay steps for samples to maximize performance. An analysis system 100 may include three resources A, B, and C. The three resources may be, for example, a vortexer, a pipette, and a heat plate. Assays 1, 2, and 3 require the use of the three resources in the order of A, B, and C, A, C, and B, and B, A, and C. To maximize performance, assay steps for different assays that require the same resources may be batched together. FIG. 11 illustrates three possible orders of performance of assay steps. As shown in FIG. 11, the order of performance (1) requires a longer running time compared to the order of performances (2) and (3). However, the order of performance (1) may maximize the performance metric if a rush instruction includes assay 1. In FIG. 11, steps of the assays requiring resource B may be batched to minimize the total running time while performing the rush instruction first.

The orders of performance (2) and (3) are shown to require the same running time. The order of performance that maximizes the performance metric may be the order of performance (2) if the performance metric is time-based and the assay steps that require resources A, B, and C must be performed consecutively. The order of performance that maximizes the performance metric may be the order of performance (3) if the performance metric is energy-based and resource B uses more energy than resource C.

Determining an Updated Assays or Assay Steps Order

Figure 12:
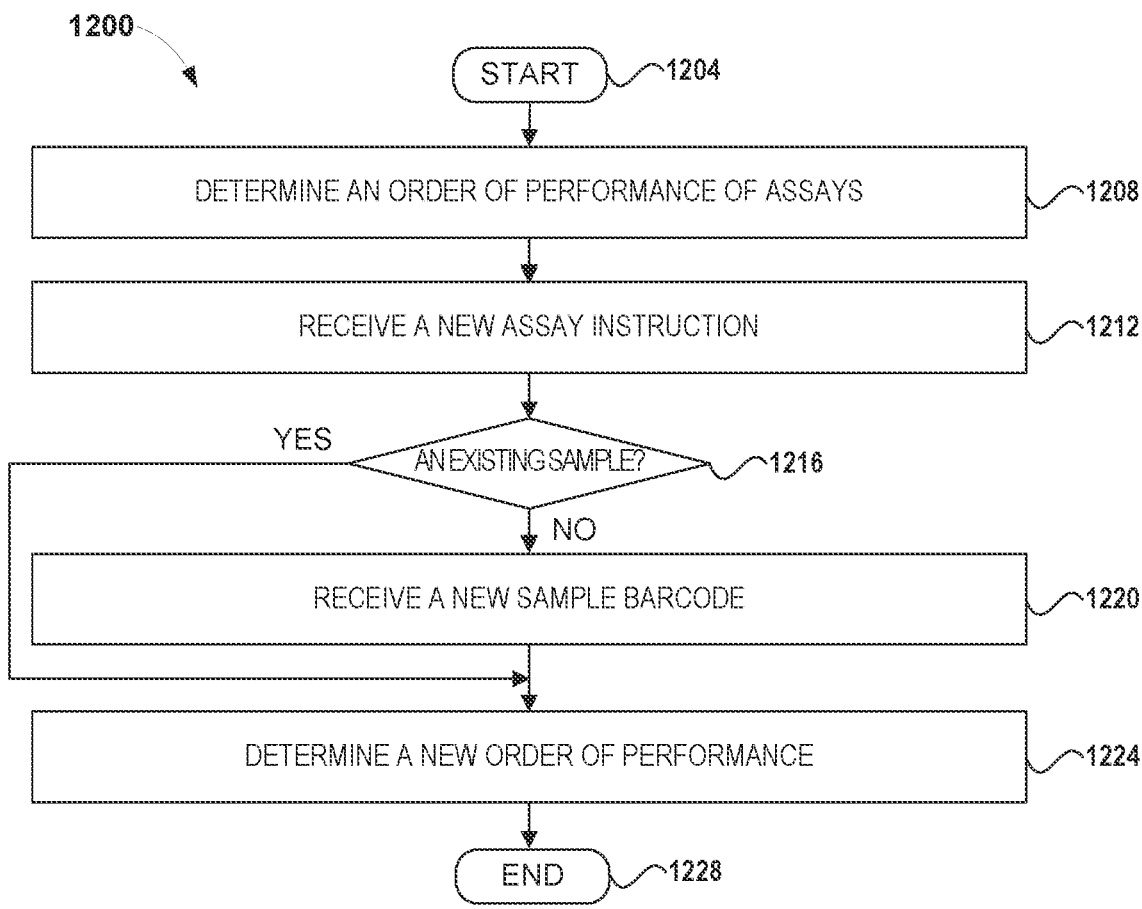
FIG. 12 is a flow diagram of one exemplary method of determining an updated order of performance of assays or assay steps after receiving a new assay instruction in an analysis system.

After the orchestration core application 220 determines an order of performance, the analysis system 100 may receive a new assay instruction from a laboratory information system 204 or a hospital information system prior to the performance of the assays for the samples are complete. The new assay instruction may be received after or before the analysis system 100 begins processing and analyzing the samples. FIG. 12 is a block diagram of a non-limiting exemplary method 1200 of determining an updated order of performance of assays or assay steps after receiving a new assay instruction. In one implementation, the orchestration core application 220 may implement the method 1200 or a part of the method 1200. After beginning at a block 1204, the method 1200 proceeds to a block 1208, where the orchestration core application 220 determines an order of performance of assays ordered for samples. The orchestration core application 220 may determine an order of performance of assays based on the method 1000 described with reference to FIG. 10.

The method 1200 proceeds to a block 1212, wherein a new assay instruction is received. For example, the orchestration core application 220 may receive a new assay instruction from a laboratory information system 204 via the network 208. The new assay instruction received may be for a new sample or an existing sample. For example, the new assay instruction may be for an existing sample that has the analysis system 100 previously received and scanned. When the new assay instruction is received, the analysis system 100 may be in the process of performing one or more assays already ordered for the sample, or the analysis system 100 may be waiting for instrument devices 264, 268 to become available prior to performing the one or more assays already ordered for the samples. As another example, the new assay instruction may be for a sample 100 that has not been received and scanned.

The method 1200 proceeds to a decision block 1216 to determine whether the new assay instruction is for an existing sample or a new sample. If the new assay instruction is for a new sample, the method 1200 proceeds to a block 1220, where the orchestration core application 220 receives a new sample identifier, such as a barcode or a two dimensional code. For example, the analysis system 100 may receive the new sample through the input window 116 of the analysis system. The orchestration core application 220 may receive the sample code scanned using the code scanner 304. After receiving the new sample code, the method 1200 proceeds to a block 1124, where the orchestration core application 220 may determine a new order of performance. The new order of performance may be based on assays or assay steps that the analysis system 100 may perform in light of the assays or assay steps that being currently performed. Table 5 illustrates four states for assays or assay steps that may be performed concurrently in light of other assays or assay steps currently being performed. The most restrictive assays or assay steps currently being performed may affect the prospective assay or assay step. In some embodiments, the most restrictive assay or assay step that is currently being performed determines the prospective assay or assay step that may be performed. The four states in Table 5 are ordered from the least restrictive to the most restrictive. The least restrictive state is the most expensive, in terms of resources of the analysis system 100, to be performed.

TABLE 5

Assays or Assay Steps Concurrency

| Action | Description |
|---|---|
| Concurrent | A prospective assay or assay step will be allowed to start regardless of the assay or assay step that is being performed currently. The prospective assay or assay step may pause to acquire common resources while being performed. |
| Shutdown | The assay or assay step being performed currently is allowed to proceed until next logical shutdown point is reach. A prospective assay or assay step will be held off until shutdown is complete. |
| Subsequent | The assay or assay step being performed currently will complete before a prospective assay or assay step will be allowed to start. |
| N/A | The option to start the prospective assay or assay step should not be available while the in light of the assay or assay step that is being performed currently. |

At the decision block 1216, if the new assay instruction is for a new sample, the method 1200 proceeds to the block 1220, where the orchestration core application 220 may determine a new order of performance. The orchestration core application 220 may determine a new order of performance of assays based on the method 1000 described with reference to FIG. 10. The method ends at a block 1228. The new order of performance determined may be to maximize a performance metric, such as the time or energy required to complete the assays, or the priorities of the assays.

In one implementation, the method 1200 may determine a new order of performance for the existing samples and the new sample prior to receiving the new sample code at the block 1120. The method 1200 may continuously determine a new order of performance until the new sample code is received. Thus, when the analysis system 100 receives the new sample and the method 1200 receives the new sample code, the analysis system 100 may continue to perform assays to maximize performance without any time delay required to determine a new order of performance.

Determining an Order of Performance of Assays or Assay Steps

The orchestration core application 220 may determine an order of performance of assays or assay steps based on the samples received, the assays ordered, availabilities of resources 248, 252, and operational states of electronic instruments 264, 268.

Figure 13:
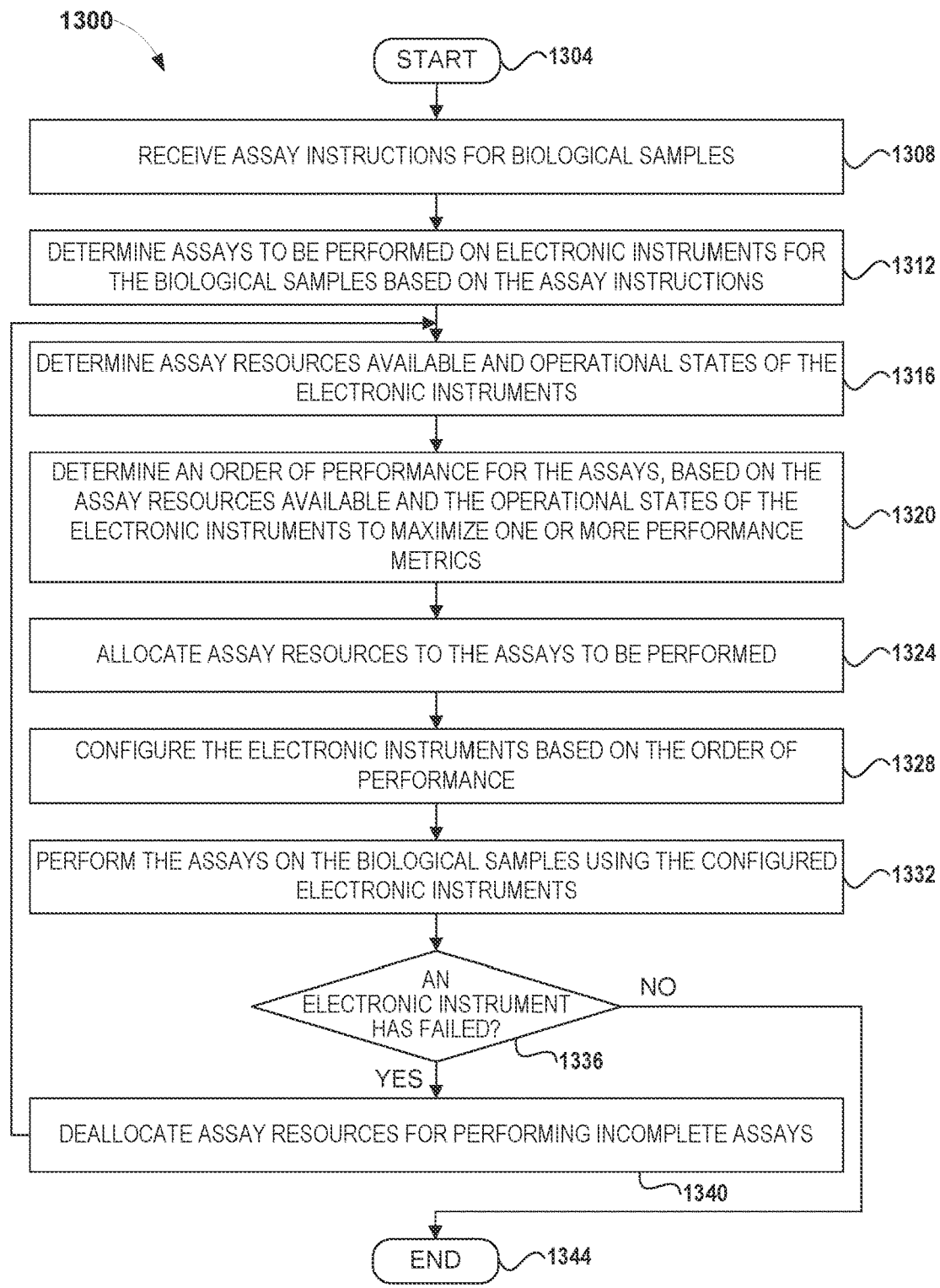
FIG. 13 is a flow diagram of one exemplary method of determining an order of performance and an updated order of performance of assays or assay steps to maximize a performance metric.

FIG. 13 is a flow diagram of one exemplary method 1300 of determining an order of performance and an updated order of performance of assays or assay steps to maximize one or more performance metrics. In one embodiment, the orchestration core application 220 may implement the method 1300 or a part of the method 1300. After beginning at a block 1304, the method 1300 proceeds to a block 1308, where the orchestration core application 220 receives assay instructions for biological samples of one or more subjects, such as patients. The assay instructions can include performing one or more assays on each of one or more biological samples. For example, the assay instructions can include performing complete blood count (CBC), blood chemistry tests, blood enzyme tests, and blood tests to assess a heart disease risk for a sample of a subject and performing the blood tests to assess the heart disease risk. The orchestration core application 220 may receive assay instructions from an instruction provider, such as a healthcare provider or laboratory personnel, such as a laboratory technician.

After receiving assay instructions, the method 1300 proceeds to a block 1312, where the orchestration core application 220 determines assays to be performed on electronic instruments 264, 268 for the biological samples based on the assay instructions. Determining the assays to be performed can comprise retrieving information relating to the assays from a database of a laboratory information management system.

The method 1300 proceeds from the block 1312 to a block 1316, wherein the orchestration core application 220 determines assay resources available and operational states of the electronic instruments 264, 268. The assay resources can include a diluent, a reagent, an assay control sample, a pipette tip, a sample tube, an extraction tube, a polymerase chain reaction (PCR) plate, space available in a waste container, or any combination thereof.

At a block 1320, the orchestration core application 220 can determine an order of performance for the assays. For example, the order of performance can be based on the assay resources available and the operational states of the electronic instruments 264, 268 determined at the block 1316. The orchestration core application 220 can determine the order of performance to maximize one or more performance metrics of the analysis system 100. In one implementation, the orchestration core application 220 can optionally receive sample scan codes to determine the samples that have received and determine the order of performance for the received samples.

The performance metrics for the electronic system can comprise, or determined based on, a number of valid assay results per time period. The number of valid assay results can be determined based on biochemical stability of the biological sample and biochemical stability of an assay resource per time period (such as one eight-hour shift, a 24-hour time period, one week, or more). For example, a performance metric can be determined based on the number of usable assay results per period of time. For example, the number of valid assay results can be optimized or maximized to ensure generation of assay results prior to the end biochemical stability. Performing all steps of an assay are performed on a biological sample does not guarantee clinically usable result. Various factors can invalidate the result. For example, the orchestration core application 220 may track the biochemical lifetime of inventory and samples in various states of assay protocol execution. Exceeding these limits of lifetime may result in indeterminate results of the assay and therefore lower the throughput of the machine. Therefore, the orchestration core application 220 may track the viability of the patient sample, assay controls, assay reagents, etc. These lifetimes change as the assays are performed and the biochemistry of the samples are altered by the assay steps. The orchestration core application 220 can plan to ensure completion of all assays or assay steps once started and before patient samples expire.

A performance metric can include the number of biological samples tested per a unit time period. For example, the primary metric can be the number of samples tested per period of time, such as the number of samples tested per day. The orchestration core application 220 can attempt to keep all analytical modules 268 and submodules and the pre-analytical modules 264 and submodules busy. The full utilization of these hardware resources can help the system achieve its maximum throughput. Idle time of any module or submodule can negatively impact the overall performance.

In one implementation, a performance metric comprises the labor or time of laboratory personnel required to operate the analysis system 100 per unit time period. The orchestration core application 220 can track a sample throughout its processing. The orchestration core application 220 may track the samples across conversions to different containers and across different modules: analytical modules, analytical submodules and the pre-analytical module. Therefore, laboratory personnel can be freed from this responsibility and human error can be removed from the processing chain. Further laboratory personnel can query the location and assay progress of a patient sample. If multiple assays are ordered for a single patient sample, the orchestration can coordinate and track the executions of multiple assays without need for laboratory personnel to intervene. A performance metric may comprise a maximum amount of time the electronic system requires no input of the laboratory personnel and/or a minimum number of times the electronic system requires the input of the laboratory personnel per time period. For example, the performance metric may be determined based on the maximum time allowed before a user must return to the system, the minimum number of times a user must return to the system within a given period of time.

The labor required can also be determined based on a number of interrupts of the electronic system per time period. For example, the second most important metric used by the system may be the required labor to operate the analysis system 100. The analysis system 100 can be designed to minimize the number of interrupts of a laboratory personnel per shift. By grouping the quantity of human operations together, the interrupt of particular laboratory functions can be minimized. This is balanced against achieving the highest throughput possible which may require an operator to keep the instruments stocked and prepared for more assays.

A performance metric can be determined based on one or more pre-determined conditions, such as an urgency of an assay, a profile of a subject, an identity of the instruction provider, or a combination thereof. The conditions may be determined by the urgency of assays specified a service level agreement. For example, the urgency of an assay to be performed or test to be completed may be from a clinical practice perspective, such as the urgency in patient management. As another example, the urgency of an assay to be performed may be determined based on the patient profile, such as patient demographics, and statistical attributes of the assay and the subject. For example, the urgency of the assay to be performed may be affected by business processes of the laboratory operating the system and the need to fulfill service level agreements between the laboratory and instruction providers, such as laboratory customers. As another example, the condition may be an one-time event, such as a sample is temporarily misplaced by laboratory personnel.

In one embodiment, the performance metrics comprise a weighted matrix with the number of valid assay results per unit time period, the number of biological samples tested per unit time period, the labor required to operate the electronic system per unit time period, and/or other variables or factors disclosed herein, weighted in ascending order or descending order. In one embodiment, the performance metrics comprises a metric corresponding to the duration of an assay, priority of a biological sample, biochemical stability of each biological sample, state of the electronic instrument, concurrency of the plurality of assay resources required for performing the plurality of assays, or any combination thereof. In another embodiment, the performance metrics reflects predetermined guidelines for the samples and assays. For example, an assay order may include parameters such as result urgency, sample expiration, user defined parameters, etc. The performance metrics can reflect such parameters. Laboratory personnel can change the priority of an individual sample or a group of samples to be processed.

Determining the order of performance can comprise determining the order of performance for the one or more assays based on the available assay resources. The orchestration core application can consider inventories available, operational states of the hardware components, patient ordered assays, samples availability, sample age, batches already in process, availability of analytical modules, analytical submodules and the pre-analytical module, biochemical stability and/or laboratory business practices. Efficient orchestration can minimize consumable expenditures, idle analytical modules, analytical submodules and the pre-analytical module, and indeterminate results.

Determining the order of performance can comprise organizing the plurality of biological samples into a plurality of sample batches. The electronic instrument can be configured to process a batch of samples at the same time. An assay resource can be configured for the electronic instrument to process the batch of samples at the same time. For example, thermocycling performance requires like assays because all samples are exposed to the same temperature variations and frequencies. Therefore, samples can be organized into batches. The consumables and the instrument devices 264, 268 can be designed to process samples in discrete batch sizes per assay. For example, the instrument devices 264, 268 can be designed to process 96 samples in a 96-well plate format. Thus, to maximize the overall throughput, each patch for an assay should include 96 samples.

At a block 1324, the orchestration core application 220 can allocate assay resources to the assays to be performed. The orchestration core application 220 can track the assay resources available and notify laboratory personnel when an assay resource is unavailable or is expected to be unavailable. For example, the orchestration core application 220 can track current level of consumable inventory in each analytical module and the pre-analytical module. The orchestration core application 220 knows the quantity already allocated to batches in process. It knows the quantities of consumable inventory required for a batch of each assay type. This knowledge allows the orchestration core application 220 to make decisions about which samples should be processed and when to start.

After allocating the assay resources, the method 1300 can proceed to a block 1328, where the orchestration core application 220 can configure the electronic instruments 264, 268 based on the order of performance determined at block 1320. For example, the orchestration core application 220 can schedule the electronic instruments 264, 268 to perform the assays based on the order of performance determined at the block 1320.

At block 1332, the analysis system 100 can perform the assays on the biological samples using the electronic instruments configured based on the order of performance. The orchestration core application 220 can keep track of the operational states of the electronic instruments 264, 268 while performing the assays. Modular assay instruments are complex machines. The electrical, mechanical and pneumatic systems may fail. To achieve the highest sample per day metric, the orchestration core application 220 can monitor equipment health and adapts the execution of assay to the operational hardware. For example, the orchestration core application 220 can monitor operational states of the electronic instruments 264, 268. The operational states of the electronic instruments 264, 268 can include a failed status, an offline status, an online status, a paused status, a power off status, a busy status, an idle status, or any combination thereof. When the orchestration core application 220 determines or receives an indication that the operational status of one of the electronic instruments 264, 268 is the failed status, the orchestration core application 220 can notify laboratory personnel of the failed status.

Alternatively or additionally, the orchestration core application 220 can notify laboratory personnel when and what to restock in the analysis system 100. Inventory items include diluents, reagents, assay control samples, pipette tips, sample tubes, extraction tubes and PCR plates. The resources available can include space available in the various waste containers.

At a decision block 1336, if the operational state of one of the electronic instruments 264, 268 is the failed status, the method 1300 proceeds to the block 1340, where the orchestration core application 220 deallocates assay resources allocated for performing assays that have not been completed. After deallocating the assay resources, the method 1300 proceeds to the block 1316, where the orchestration core application 220 can determine the updated assay resources available and the updated operational states of the electronic instruments 264, 268, including the unavailable operational state of one of the electronic instruments 264, 268, at the block 1316 and determine an updated order of performance of the incomplete assays based on the updated assay resources available and the updated operational states of the electronic instruments 265, 268. In one embodiment, the orchestration core application 220 continuously determines an updated order of performance and de-allocates and allocates resources. The updated order of performance can be based on the operational states of the electronic instruments 264, 268, the resources available, and new assay instructions and new samples received.

If the operational states of the electronic instruments 264, 268 during the performance of the assays do not include the failed status, the analysis system 100 can continue performing the assays on the biological samples until all assays or assay steps are completed, where the method 1300 ends at a block 1344.

Figure 14:
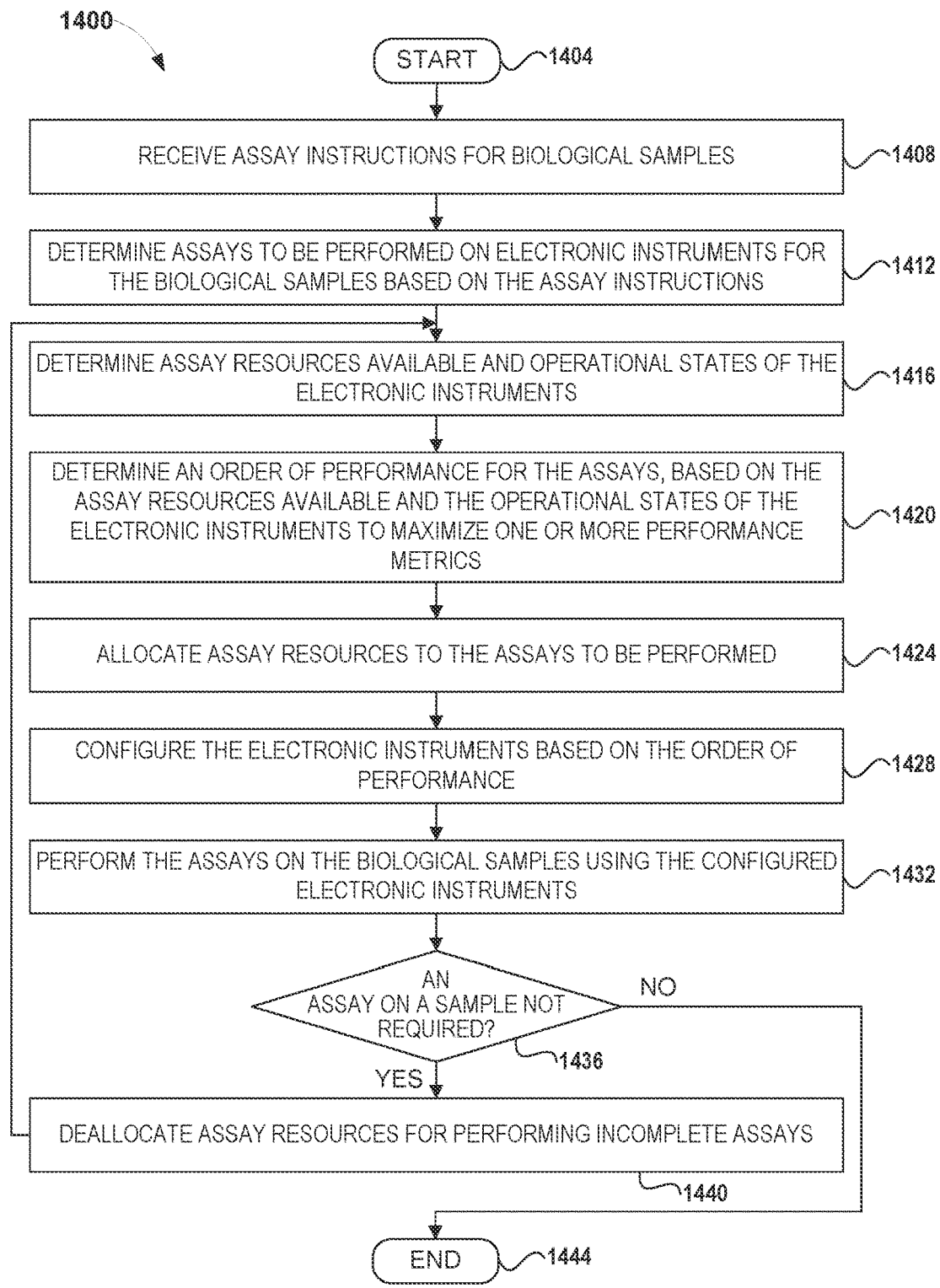
FIG. 14 is a flow diagram of another exemplary method of determining an order of performance and an updated order of performance of assays or assay steps to maximize a performance metric.

FIG. 14 is a flow diagram of one exemplary method 1400 of determining an order of performance and an updated order of performance of assays or assay steps to maximize one or more performance metrics. In one embodiment, the orchestration core application 220 may implement the method 1400 or a part of the method 1400. After beginning at block 1404, the method 1400 may proceed to blocks 1408, 1412, 1416, 1420, 1424, 1428, and 1432 as described with reference to blocks 1308, 1312, 1316, 1320, 1324, 1328, and 1332.

At a decision block 1436, the orchestration core application may determine that an assay on a sample is no longer required. Then method 1400 may proceed to a block 1440, where the orchestration core application deallocates assay resources allocated for performing assays that have not been completed as described with reference to block 1340 in FIG. 13. For example, the orchestration core application may receive a result of an assay on a biological sample determined using one or more of the electronic instruments using the ordered determined. The orchestration core application can determine a second assay of the biological same or another biological sample needs not be performed. For example, a unit of work, which may include one or more assays, can be cancelled due to inferred results from a prior assay result. Such cancellation may result in cost savings or time sayings since the second/pending assay no longer needs to be performed. The orchestration core application may determine that a pending assay is no longer relevant to a clinical diagnosis via a set of rules. For example, a first cheaper assay for determining a physiological condition or state may have a low false positive rate and a high false negative rate, and a second more expensive assay for determining the same physiological condition may have a low false positive rate and a low false negative rate. Instructions received by the orchestration may include performing both assays for a sample, and the orchestration core application may determine that the first assay should be performed before the second assay is performed. If the result of the first assay is negative, the second assay may be performed. If the result of the first assay is positive, the orchestration core application may determine that the second assay needs not be performed. The orchestration core application can determine an updated order of performance, which excludes performing the second assay on the sample, to maximize at least one performance metric of the analysis system. Resources may be deallocated based on the updated order of performance.

If all assays are required, the analysis system can continue performing the assays on the biological samples until all assays or assay steps are completed, where the method 1400 ends at a block 1444.

Additional Features

Storing of Assay Results. The analysis system 100 or 100A may perform assays based on an assay order received from the laboratory information system and an order of performance determined by the orchestration core application. Although the modules listed below relate to the analysis system 100 shown in FIG. 2A, these same assays may be performed similarly by the analysis system 100A of FIG. 2B. After completion of the assays, the analysis system 100 can send the assay results to the laboratory information system 204 via the network 208. Due to network or other problems, the analysis system 100 may be unable to establish a connection with the laboratory information system 204 via the network 208 when the assay results are available. In this embodiment, the analysis system 100 can store assay results locally and then send the results to the laboratory information system 204 once a connection is established. The analysis system 100 can attempt to reestablish a connection periodically. If no connection can be reestablished, laboratory personnel can be notified of the failed status. This notification may be, for example, an email, text, sound or other indication that the results were not sent to the laboratory information system 204. The analysis system 100 can store the assay results in an unencrypted format or an encrypted format using symmetric-key schemes.

Monitoring of Inventory and Operational Integrity. The orchestration core application 220 may determine an order of performance of assays or assay steps based on the samples received, the assays ordered, availabilities of resources 248, 252, and operational states of electronic instruments 264, 268. The orchestration core application 220, the orchestration sub-application 240 of the pre-analytical instrument 104, or the orchestration sub-application 244 of the analytical instruction 108 may keep track of assay resources available. The assay resources may include consumables 256, 268 and reagents 272, 276. The assay resources can include a diluent, a reagent, an assay control sample, a pipette tip, a sample tube, an extraction tube, a polymerase chain reaction (PCR) plate, space available in a waste container, or any combination thereof.

Modular assay instruments are complex machines. The electrical, mechanical and pneumatic systems may fail. To achieve the highest performance, the orchestration core application 220 can monitor the equipment health and integrity of the electronic instruments 264, 268 and adapt the execution of each assay being performed to the operational hardware. For example, the orchestration core application 220 can monitor operational states of the electronic instruments 264, 268. The operational states of the electronic instruments 264, 268 may include a failed status, an offline status, an online status, a paused status, a power off status, a busy status, an idle status, or any combination thereof. As another example, the analysis system 100 can include an externally or internally mounted un-interruptible power supply (UPS). The orchestration core application 200 may monitor the health of the UPS. When the orchestration core application 220 determines or receives an indication that the operational status of one of the electronic instruments 264, 268 is the failed status, the orchestration core application 220 can notify laboratory personnel of the failed status.

The analysis system 100 can generate a report of the inventory and the operational integrity of the electronic instruments 264, 268. For example, when the orchestration core application 220 determines that a component of an electronic instrument 264, 268 has a failed status, the analysis system 100 can generate a report with diagnostic data and codes indicating that the particular component has failed and needs to be serviced or replaced. The orchestration core application 220 can re-determine an order of performance based on the failure. Some assays may be paused and restarted while other assays may be repeated.

The orchestration core application 220 can coordinate the operations of multiple independent, but connected, instruments that require availability of hardware and consumables across these instruments to correctly prepare and analyze a single sample. The independent and connected instruments may include the pre-analytical instrument 104, the analytical instrument 108, and the instrument devices 264, 268. For example, to perform an assay on a sample, the sample may have to be pipetted. If any of the pipette robots or pipette tips of the pre-analytical instrument 104 or the consumables 268 and reagents 276 of the analytical instrument 108 are not available, the orchestration core application 220 may determine an order of performance to exclude the assay being performed on the sample.

Status indicators. The analysis system 100 can include multiple visual indicators across multiple independent but connected instruments. The analysis system 100 can use the visual indicators to indicate to users of the system 100 that user attention is needed by the system 100. For example, a visual indicator associated with the analysis system 100 may flash red when there is an overall system failure. As another example, an indicator associated with the pre-analytical system 104 may flash yellow when consumables 256, such as pipette tips, need to be refilled soon.

Log. The analysis system 100 may aggregate and store log files of the multiple independent but connected instruments for later retrieval. For example, the analysis system 100 may aggregate and store log files of the assays performed, the operational states of the instruments 104, 108 and devices 264, 268, and the levels of the consumables 256, 268 and reagents 272, 276. As another example, the log files can include results or intermediate results of the assays being performed. The analysis system 100 may transfer the log file data to a central or remote data storage device to allow remote troubleshooting via analysis of the logs. For example, when a component of the pre-analytical instrument 104 has a failed status, the analysis system 100 can retrieve a log file containing such failed status from the pre-analytical instrument 104 and transfer the log file to the laboratory information system 204 for diagnosis of the failed status. The log file information may be transferred based on the importance or the timing of the log file information. For example, log file information containing a failed status of the overall analysis system 100 may be prioritized over log file information indicating that consumables should be refilled soon.

Determining Operating Coordinates and Parameters. The instrument devices 264, 268 may include physical hardware components such as motor encoders, integrated circuits, solenoids, and the like so the orchestration core application 220 is able to track the operational state of the hardware in each instrument. In one implementation, the instrument devices 264, 268 may include interactive position probes and cameras, and the orchestration core application 220 can determine correct operating coordinates and parameters of the instrument devices 264, 268 or components thereof. For example, the pre-analytical instrument 104 may include a pipette robot with a position probe. The pre-analytical instrument 104 may include a camera that captures images of the position probe. The orchestration core application 220 can determine the coordinates and the parameters of the pipette robot using the images of position probe. As another example, the pipette robot can include multiple position probes and the pre-analytical instrument 104 can include three cameras that are orthogonal to one another. The orchestration core application 220 can determine the coordinates and the parameters of the pipette robot in three dimensions using the images captured by the orthogonal camera. The images captured may also be used to calibrate the components of the instrument devices 264, 268. The position probes may be fixed or movable on the components. Fewer movable position probes may be need to determine the operating coordinates and parameters of the components. The position probes may use different colors to indicate its status, such as in use or failed.

Un-Interruptible Power Supply. The analysis system 100, the pre-analytical instrument 104, the analytical instrument 108, or the instrument devices 264, 268 may include an externally or internally mounted un-interruptible power supply (UPS). In the event of a power failure, the UPS may provide the analysis system 100 or its components sufficient power to ensure that all data is stored to a durable storage device, such as a Solid State Drive (SSD) or Hard Disk Drive (HDD). The data stored to the durable storage device in the event of power failure can include results or intermediate results of the assays being performed. The data may include states and parameters of the analysis system 100 and its components.

Video Surveillance. The analysis system 100 can include internal cameras that capture video surveillance data of the inner workings of the system 100. The analysis system 100 may store the video surveillance data and display the video on demand to a user or technician of the system 100. In one embodiment, the video surveillance data is stored in a durable internal storage device for later retrieval.

For example, laboratory personnel, or a technician, may want to review a video captured when a failed status of a component of the analysis system 100 is detected. As another example, laboratory personnel may want to review a video tracking a sample of interest to ensure that no tampering occurred with the sample. The analysis system 100 may automatically package the video with logs and other data to support remote evaluation of errors or issues.

Coordinating with Other Computer Systems or Sub-Systems. In one embodiment, the orchestration core application 220 can coordinate with other systems associated with the analysis system 100. For example, the orchestration core application 220 can determine an order of performance based on the operational states of the pre-analytical instrument 104 and the analytical instrument 108. As another example, the orchestration core application 220 of one analysis system 100 can determine an order of performance based on the operational state of another analysis system 100. In one embodiment, the orchestration sub-application 240 of the pre-analytical instrument 104 can affect the order of performance determined by the orchestration core application 220 for the pre-analytical instrument 104 and the analytical instrument 108, and vice versa.

Worklists of Samples. The orchestration core application 220 may automatically build and release worklists of samples for processing as groups of samples present that correspond to the nominal operation of the analysis system 100 or its components. For example, the orchestration core application 200 may automatically build and release worklists of samples for processing as groups of samples present that correspond to the nominal operation of the device and according to user defined rules based on day of the week, day of the month, time of day, or any combination of the above. As another example, the orchestration core application 220 may automatically build and release worklists of samples present for processing as groups of samples that correspond to the nominal operation of the device and according to user defined rules based on day of the week, day of the month, time of day, or any combination of the above as applied to a specific test that has been order for each sample.

Sample Removal. The orchestration core application 220 can monitor the processing and analysis of a sample and alert laboratory personnel when the original sample container that is being removed or has already been removed by the laboratory personnel should be retrieved for further review and evaluation. For example, the orchestration core application may alert the user when the original sample container that has already been removed from the system should be retrieved for further review and evaluation and provide the laboratory personnel sample information and location for ease sample retrieval. The sample information and location may include a sample identifier and a location of the sample, such as a location on a rack. The orchestration core application 220 can re-determine an order of performance when the sample is returned to the analysis system 100.

Cloud-Based Orchestration Core Application

Figure 15:
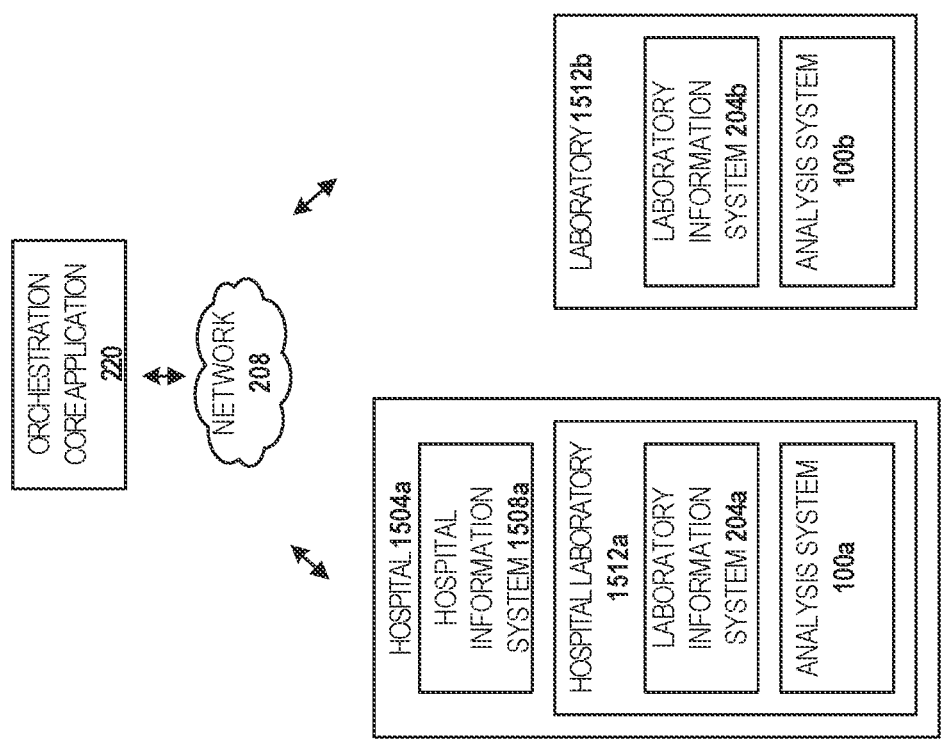
FIG. 15 is a block diagram of an orchestration core application in communication with hospital and laboratory information systems and analysis systems over a network.

FIG. 15 is a block diagram of an analysis system in communication with a laboratory information system and analysis systems over a network. A hospital 1504a may include a hospital information system 1508a that stores and processes hospital data. For example, the hospital information system 1508a may store patient data and prescription ordering information. The hospital 1504a may also have an onsite hospital laboratory 1512a with a laboratory information system 204a and an analysis system 100a. The laboratory information system 204a may receive assay instructions 212 and patient information from the hospital information system 1508a. The laboratory information system 204a may store the requirements of the assays that the analysis system 100a is capable of performing. The analysis system 100a may be capable of performing certain assays such as a general cancer panel. Although the orchestration core application 220 is shown to control two analysis systems, the orchestration core application 220 is capable of controlling numerous analysis systems with different capabilities situated at different geographical locations. The analysis systems 100a, 100b may be the analysis system of FIG. 2A and/or FIG. 2B.

A laboratory 1512b, such as an independent laboratory, may include a laboratory information system 204b and an analysis system 100b. The laboratory information system 204b may store the requirements of the assays that the analysis system 100a is capable of performing. The capability of the analysis system 100b and the capability of the analysis system 100a may be the same or different. For example, the analysis system 100b of the laboratory 1512b may be capable of performing a general cancer panel and a specialized cancer instruction.

To determine an order of performance for the analysis system 100a or the analysis system 100b, the orchestration core application 220 may receive assay instructions from the hospital information system 1508a, the laboratory information system 204a, or the laboratory information system 204b. The orchestration core computing application 220 may keep track of the capabilities of the analysis systems 100a, 100b. For example, a resource of the analysis system 100a may become temporarily available, and the analysis system 100a may provide the orchestration core application 220 with this information.

Given the assay instructions received or the samples scanned, the orchestration core application 220 may determine orders of performance for the analysis systems 100a, 100b, to maximize a performance metric. For example, the hospital 1204a may prefer that its analysis system 100a performs as many assays as possible in order to minimize cost. However, depending on the availability and capability of the analysis system 100a, the orchestration core application 220 may determine that certain assays or certain assays for certain samples should be performed by the analysis system 100b.

As another example, an assay instruction may state that a specialized cancer panel should be performed after a general cancer panel determines that a patient is at risk of a cancer. The initial orders of performance for the analysis systems 100a, 100b determined by the orchestration core application 220 may include the general cancer panel being performed by the analysis system 100a of the hospital 1504a. The orders of performance for the analysis systems 100a, 100b may be determined using the methods 1000 and 1200 described with reference to FIGS. 10 and 12 respectively. If the result of the general cancer panel indicates that the patient at risk of a cancer, the orchestration core application 220 may determine a new order of performance for the analysis system 100c of the laboratory 1512b. This new order of performance may take into account of the time required to transport the sample from the hospital 1504a to the laboratory 1512b. The orchestration core application 220 may determine the new order of performance using the methods 1000 and 1200 described with reference to FIGS. 10 and 12 respectively. For example, the analysis system 100b may be performing assays for other samples when the result of the general cancer panel becomes available. The new order of performance for the analysis system 100c may be determined to maximize the performance of the analysis system 100c or the combined performance of the analysis systems 100a, 100b.

In one embodiment, the orchestration core application 220 may receive an indication that the analysis system 100b becomes unavailable. The analysis system 100b may become unavailable if the connection of the orchestration core application 220 to the analysis system 100b is lost or performing a rush assay instruction. Based on the unavailability of the analysis system 100b, the orchestration core application 220 may determine a new order of performance for the analysis system 100a. In one embodiment, the orchestration core application 220 determines orders of performance for some analysis systems in order to maximize a performance metric with respect to these analysis systems to increase the overall efficiency of handling assay samples. For example, the hospital 1504a may have a contractual relationship with the laboratory 1512b such that orders of performance for analysis systems 100a, 100b are determined to maximize a performance metric with respect to these two analysis systems 100a, 100b.

Figure 16:
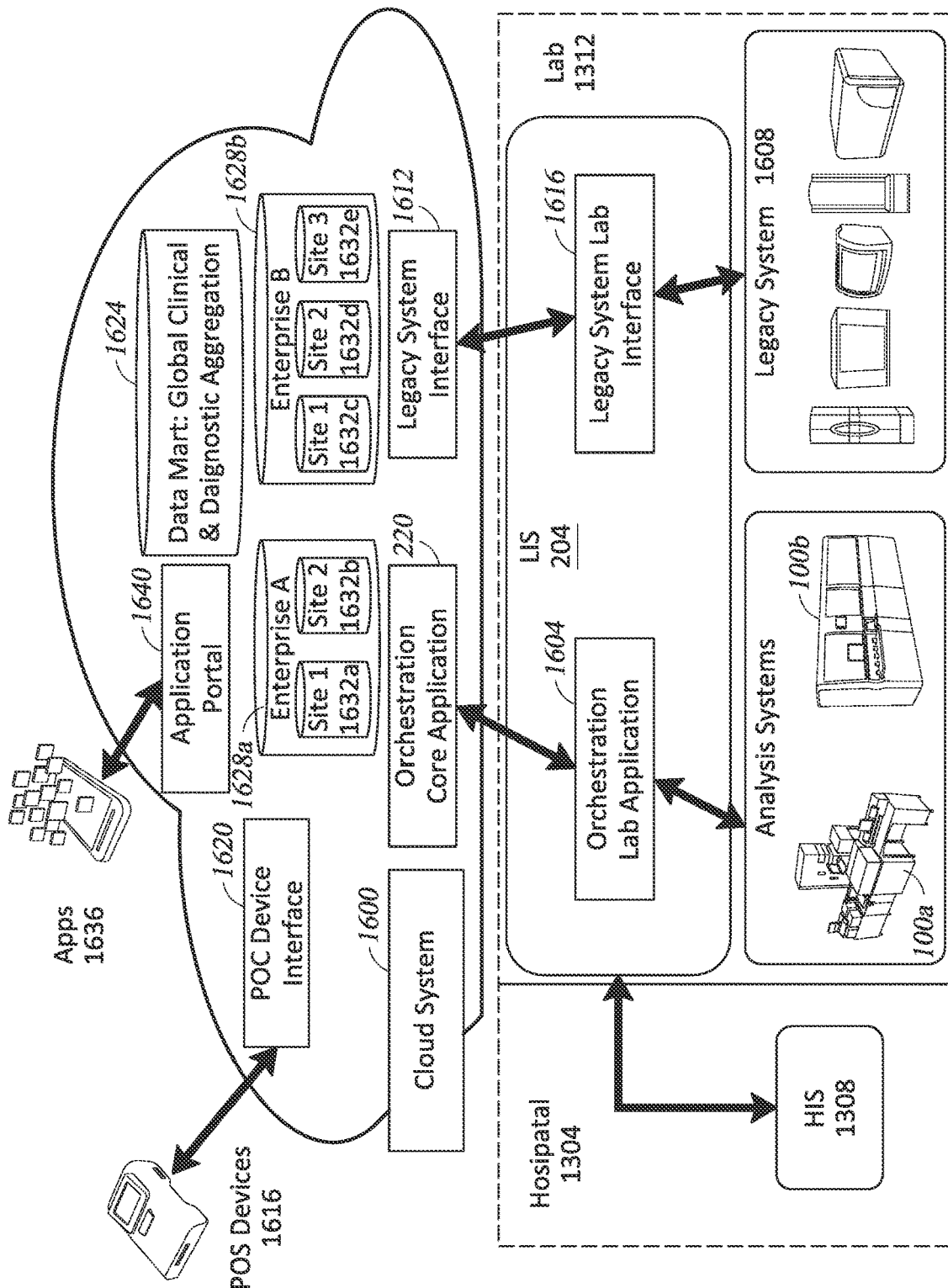
FIG. 16 is a schematic illustration of a cloud server-based orchestration core application in communication with an orchestration laboratory application to coordinate automated sample processing and analysis.

FIG. 16 is a schematic illustration of an orchestration core application stored in a cloud-based server in communication with an orchestration laboratory application to coordinate automated sample processing and analysis. A hospital 1504 may include a hospital information system 1508 that stores and processes hospital data. For example, the hospital information system 1508 may store patient data and prescription ordering information. The hospital 150a may have an onsite hospital laboratory 1512 with a laboratory information system 204 and multiple analysis systems 100a, 100b. The laboratory information system 204 may receive assay instructions and patient information from the hospital information system 1508. The laboratory information system 204 may store the requirements of the assays that the analysis systems 100a, 100b are capable of performing.

An orchestration core application 220 on a cloud system 1600 can communication with an orchestration laboratory application 1604 on the laboratory information system 204 to coordinate automated sample processing and analysis using the analysis systems 100a, 100b. When the orchestration core application 220 is available, the orchestration laboratory application 1604 may send the assay instructions received or the samples scanned to the orchestration core application 220. Based on the information received from the orchestration laboratory application 1604 and similar information received from other orchestration laboratory application, the orchestration core application 220 may determine orders of performance for the analysis systems 100a, 100b controlled by the orchestration laboratory application 1604 and analysis systems controlled by other orchestration laboratory systems. Consequently, the orders of performance determined by the orchestration core application 220 can maximize a performance metric given the assay instructions received or the samples scanned. When the orchestration core application 220 is unavailable, the orchestration laboratory application 1604 may be capable of determining orders of performance for the analysis systems 100a, 100b, to maximize a performance metric given the assay instructions received or the samples scanned.

With this distributed architecture, the orchestration core application 220 and the orchestration laboratory application 1604 may maximize a performance metric given the information and resources available. For example, orders of performance determined by the orchestration core application 220 may be based on the capabilities of the analysis systems 100a, 100b in the laboratory 1512 and another laboratory. Each laboratory has an analysis system capable of performing a general cancer panel. However, performing the general cancer panel using the analysis system in the laboratory 1512 may be more costly. To reduce the cost of performing the cancer panel, the orchestration core application 220 may determine that the general cancer panel been performed using an analysis system of the other laboratory. Prior to the sample (or a portion of the sample) for the cancer panel is sent to the other laboratory, the orchestration laboratory application 1604 may lose its connection to the orchestration core application 220. Because the orchestration laboratory application 1604 is uncertain of whether the general cancer panel can be completed even if the sample (or a portion of the sample) is sent to the other laboratory, the orchestration laboratory application 1604 can determine a new order of performance for the analysis systems 100a, 100b.

In one embodiment, the cloud system 1600 may, via its orchestration core application 220, receive data or test results generated by the analysis systems 100a, 100b, from the orchestration laboratory application 1604. Although the orchestration core application 220 is shown to control two analysis systems 100a, 100b, the orchestration core application 220 is capable of controlling numerous analysis systems with different capabilities situated at different geographical locations.

The laboratory 1512 may include a number of legacy systems 1608 without automation capability. These legacy systems 1608 can be controlled by lab-based middleware systems providing the high availability and high performance link between the lab platforms, and the other IT systems. This may be used primarily for running the local laboratory operations. The cloud system 1600 may, via its legacy system interface 1612, receive data or test results generated by these legacy systems 1608 from a legacy system laboratory interface 1616 of the laboratory information system 204. The legacy system laboratory interface 1616 may receive data generated by the legacy systems 1608 from lab-based middleware systems. In one embodiment, the cloud system 1600 may receive data or test results generated by point-of-care (POC) devices via a POC interface.

By controlling analysis systems 100a, 100b and receiving data and test results generated by the analysis systems 100a, 100b, the legacy systems 1608, and POC devices 1615, the cloud system 1600 is capable of enterprise-wide management of related laboratory data as well as remote microbiology operations for labs. Aggregation of data across all hospitals, laboratories, and patients enables value-added services and provides insight to hospital, laboratory, and patients usages. Examples of value-added services include peer benchmarking and global surveillance. The data and test results received can be stored in a data mart capable of global clinical and diagnostic aggregation. In one embodiment, data for different hospitals, institutions, or affiliated hospitals or institutions are stored in different databases 1624a, 1624b at different locations 1632a-1632e.

Access to the cloud functionality may be provided via Apps 1636 distributed through an application portal 1640, supporting both traditional and mobile devices. The application portal 1640 may be centrally managed and redirect users to the relevant technology-specific App stores. These App stores may enable distribution of Apps 1636, possibly developed by third-party developers, that are in compliance with the architecture of the cloud system 1600. Apps 1636, possibly developed by third-party develops, may more flexibly address custom data management requirements.

In one embodiment, the cloud system 1600 takes advantage of social networking to enable better engagement of hospitals, laboratories, and patients. The cloud system 1600 may provide better Customer Relationship Management activities ranging from service and training to opportunities for inbound and outbound marketing activities.

The architecture of the cloud system 1600 is scalable to meet changing market demands. In one embodiment, the architecture supports both public and local (private) clouds, which eliminate data sovereignty objections for users that want all data behind their firewall. The cloud system 1600 is secure, thus addressing concerns regarding data, and HIPAA privacy, and regulatory compliance. The cloud system 1600 is also extensible and capable of supporting new/updated devices and modules.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for high throughput automation of biological assays on an electronic system comprising a plurality of electronic instruments, the method comprising:
   receiving sample identifiers and assay instructions for a plurality of biological samples;
   determining one or more assays to be performed on the plurality of electronic instruments for the plurality of biological samples based on the sample identifiers and the assay instructions;
   determining assay steps or assays of the one or more assays that each of the plurality of electronic instruments may perform concurrently;
   determining an order of performance for the one or more assays to maximize a performance metric for the electronic system; and
   performing the one or more assays on the plurality of electronic instruments for the plurality of biological samples based on the order of performance that maximizes the performance metric.

2. The method of claim 1, wherein the sample identifiers comprise sample codes read from a code scanner.

3. The method of claim 1, wherein the plurality of electronic instruments comprises a plurality of analytical modules and associated analytical submodules.

4. The method of claim 3, wherein the plurality of electronic instruments comprises a plurality of pre-analytical modules and associated pre-analytical submodules.

5. The method of claim 1, further comprising configuring each of the plurality of electronic instruments based on the order of performance prior to performing the one or more assays.

6. The method of claim 1, further comprising determining whether the electronic system has sufficient resources to perform the one or more assays after determining the one or more assays to be performed.

7. The method of claim 6, wherein the resources comprise one or more of a diluent, a reagent, an assay control sample, a pipette tip, a sample tube, an extraction tube, a polymerase chain reaction (PCR) plate, space available in a waste container, or any combination thereof.

8. The method of claim 6, further comprising notifying a user if the electronic system does not have sufficient resources to perform the one or more assays.

9. The method of claim 1, further comprising determining whether the conditions of the plurality of biological samples satisfy the requirements of the one or more assays after determining the one or more assays to be performed.

10. The method of claim 9, wherein the conditions of the plurality of biological samples comprise a sample volume, a sample age, a sample quality, or any combination thereof.

11. The method of claim 9, further comprising notifying a user if the conditions of the plurality of biological samples do not satisfy the requirements of the one or more assays.

12. The method of claim 1, further comprising determining whether the assay instructions include a special instruction prior to determining the order of performance.

13. The method of claim 12, wherein determining an order of performance comprises maximizing the performance metric with the special instruction prioritized.

14. The method of claim 1, wherein the performance metric comprises a time duration for performing all of the one or more assays, an energy used for performing all of the one or more assays, a quality or accuracy of assay results, or any combination thereof.

15. The method of claim 1, further comprising, after determining the order of performance:

receiving a new assay instruction and determining additional assays or assay steps to be performed based on the new assay instruction; and determining a new order of performance of the remaining one or more assays plus the additional assays or assay steps based on comparing the additional assays or assay steps with the assays or assay steps currently being performed.

16. The method of claim 15, further comprising determining whether the new assay instruction is for a new sample and receiving a new sample identifier prior to determining the new order of performance.

17. The method of claim 15, wherein the new order of performance maximizes a performance metric for the electronic system.

18. A method for high throughput automation of biological assays on an electronic system comprising a plurality of electronic instruments, the method comprising:

determining an order of performance for one or more assays to be performed on the plurality of electronic instruments for a plurality of biological samples to maximize a performance metric for the electronic system;

receiving a new assay instruction and determining additional assays or assay steps to be performed based on the new assay instruction;

determining a new order of performance of the remaining one or more assays plus the additional assays or assay steps based on comparing the additional assays or assay steps with the assays or assay steps currently being performed; and performing the remaining one or more assays plus the additional assays or assay steps on the plurality of electronic instruments for the plurality of biological samples based on the new order of performance.

19. The method of claim 18, further comprising determining whether the new assay instruction is for a new sample and receiving a new sample identifier prior to determining the new order of performance.

20. The method of claim 18, wherein the new order of performance maximizes a performance metric for the electronic system.

* * * * *